(12) United States Patent
Paulitschke et al.

(10) Patent No.: US 10,295,463 B2
(45) Date of Patent: May 21, 2019

(54) DEVICE AND METHOD FOR INVESTIGATING ONE OR A PLURALITY OF PHASE OBJECTS

(71) Applicant: Ludwig-Maximilians-Universität München, München (DE)

(72) Inventors: Philipp Paulitschke, München (DE); Joachim Radler, München (DE)

(73) Assignee: Ludwig-Maximilians-Universität München, München (DE)

( * ) Notice: Subject to any disclaimer, the term of this patent is extended or adjusted under 35 U.S.C. 154(b) by 206 days.

(21) Appl. No.: 14/539,556

(22) Filed: Nov. 12, 2014

(65) Prior Publication Data
US 2015/0140551 A1 May 21, 2015

(30) Foreign Application Priority Data

Nov. 12, 2013 (DE) .................. 10 2013 112 415

(51) Int. Cl.
*G01N 21/47* (2006.01)
*C12Q 1/18* (2006.01)
*G01N 33/50* (2006.01)

(52) U.S. Cl.
CPC .......... *G01N 21/4788* (2013.01); *C12Q 1/18* (2013.01); *G01N 33/5029* (2013.01); *G01N 2201/068* (2013.01); *G01N 2201/06113* (2013.01)

(58) Field of Classification Search
None
See application file for complete search history.

(56) References Cited

U.S. PATENT DOCUMENTS

| 4,647,544 | A | 3/1987 | Nicoli et al. |
| 5,089,387 | A | 2/1992 | Tsay et al. |
| 2002/0025534 | A1 | 2/2002 | Goh et al. |
| 2002/0037593 | A1 | 3/2002 | Craighead et al. |
| 2004/0151626 | A1* | 8/2004 | Cunningham ........ B01L 3/5085 435/287.2 |
| 2005/0068543 | A1 | 3/2005 | Angeley |
| 2010/0182606 | A1 | 7/2010 | Prenner et al. |
| 2012/0231489 | A1 | 9/2012 | Lenhert |
| 2013/0147919 | A1* | 6/2013 | Xia ................... H04N 13/0203 348/46 |
| 2014/0090487 | A1* | 4/2014 | Paulitschke ............ G01L 1/241 73/862.624 |

FOREIGN PATENT DOCUMENTS

| DE | 10 2009 019 717 A1 | 11/2010 | |
| DE | 102010007365 A1 | 8/2011 | |
| DE | 102011050493 A1 | 11/2012 | |
| EP | 0276968 A2 * | 8/1988 | ......... G01N 21/4788 |
| WO | WO20121586050 A1 * | 11/2012 | ............ G01L 1/241 |

* cited by examiner

Primary Examiner — Robert J Yamasaki
(74) Attorney, Agent, or Firm — Marshall Gerstein & Borun LLP

(57) ABSTRACT

A method for investigating one or a plurality of phase objects is described, in which a grid made up of elements is used, which is illuminated with light of a light source, the coherence length of which is larger than the average spacing of adjacent elements of the grid. A diffraction image of the illuminating light scattered on the grid is generated, whereby the one or the plurality of phase objects are placed in the light path between the light source and the grid and/or in the light path of the illuminating light scattered on the grid. At least a part of the diffraction image is detected by an optical sensor directly or after interaction with further optical components and converted into a signal. The signal is analyzed further in order to ascertain information relating to the one or plurality of phase objects therefrom. A corresponding device is likewise described.

21 Claims, 18 Drawing Sheets

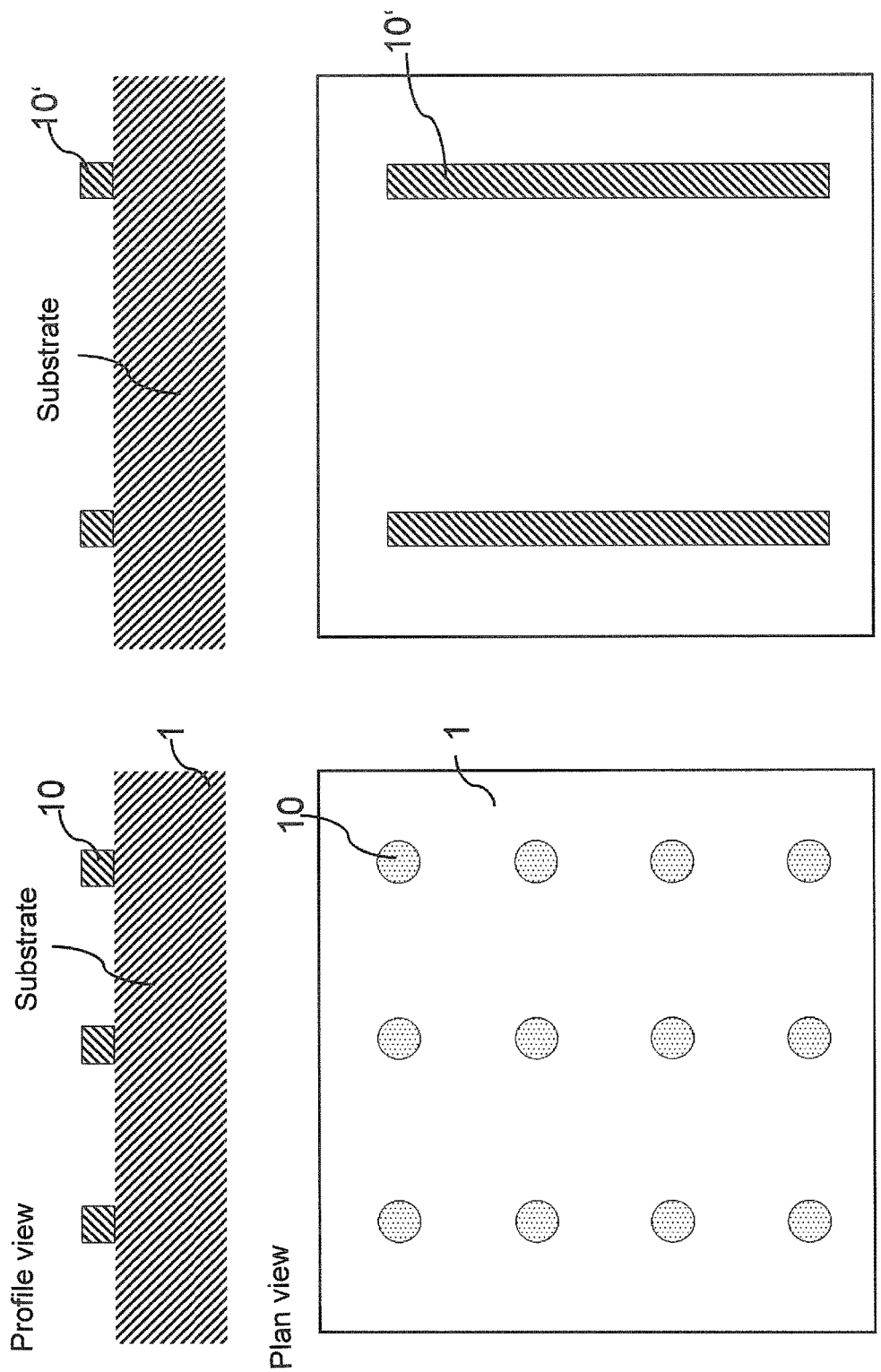

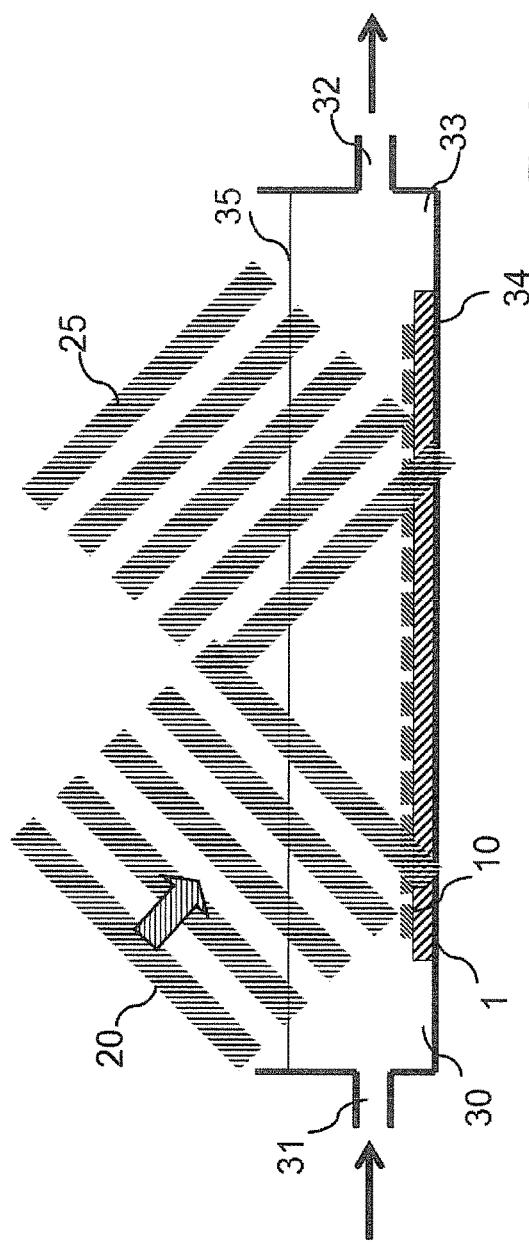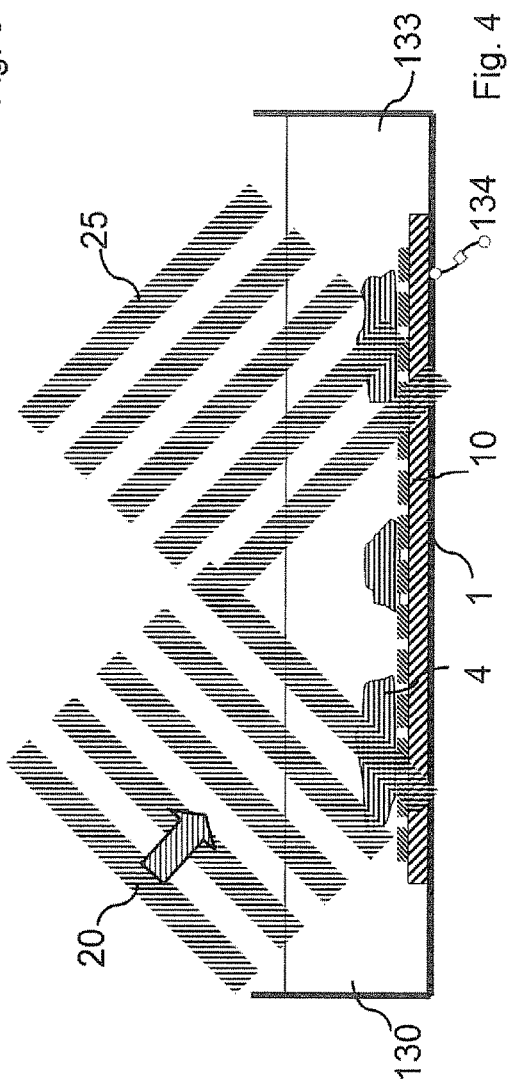

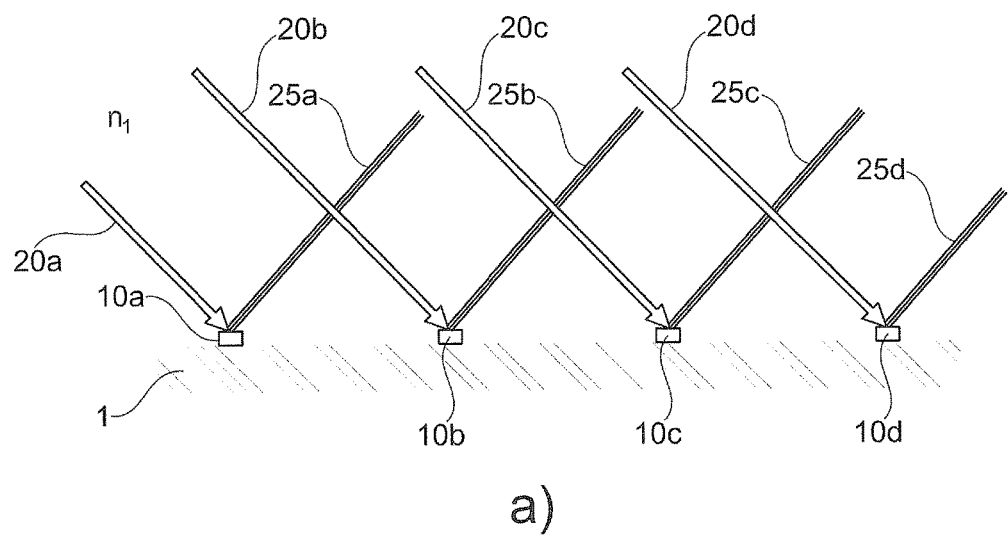
a)
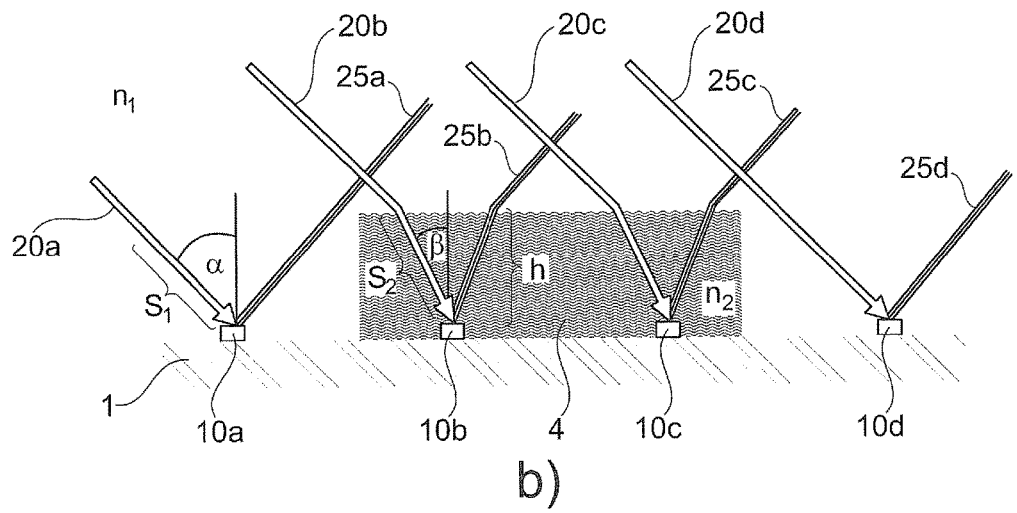
b)
Fig. 6

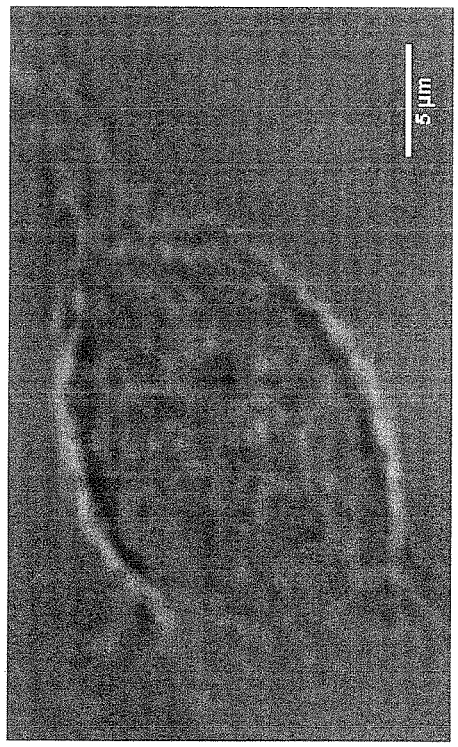
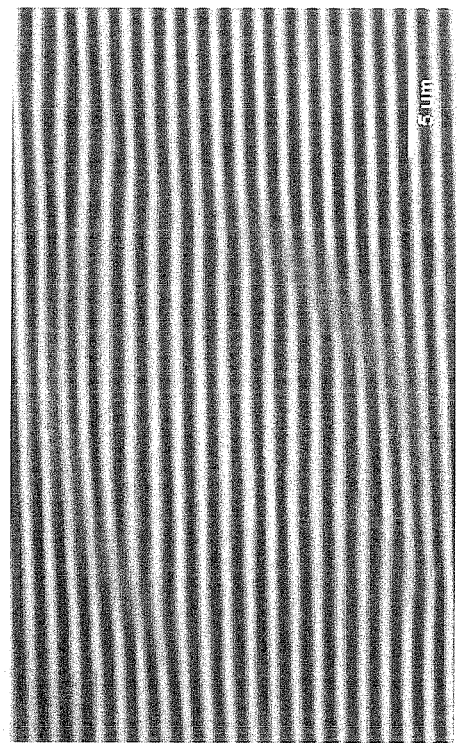
Fig. 10a
Fig. 10b
Fig. 9a — Bright field transmission microscopy
Fig. 9b — Monochromatic reflection microscopy a) b)

Figure 19:
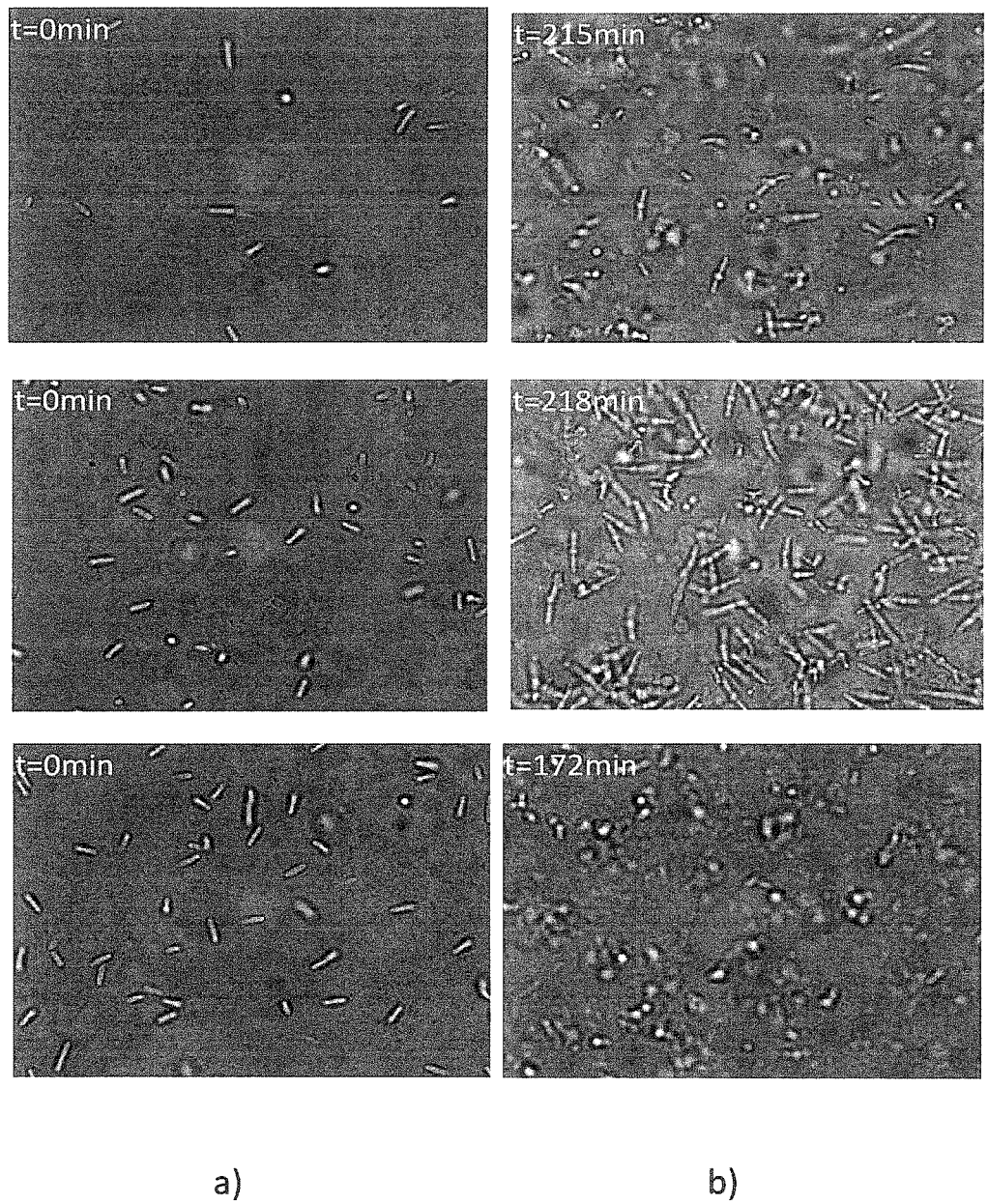

Fig. 19
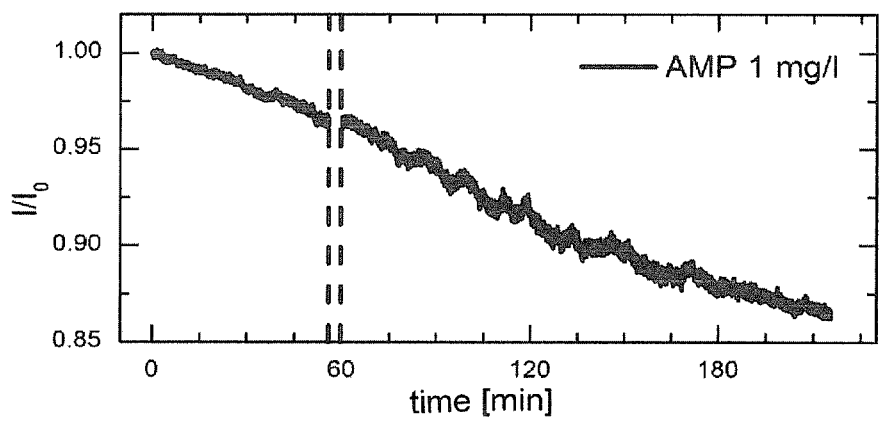
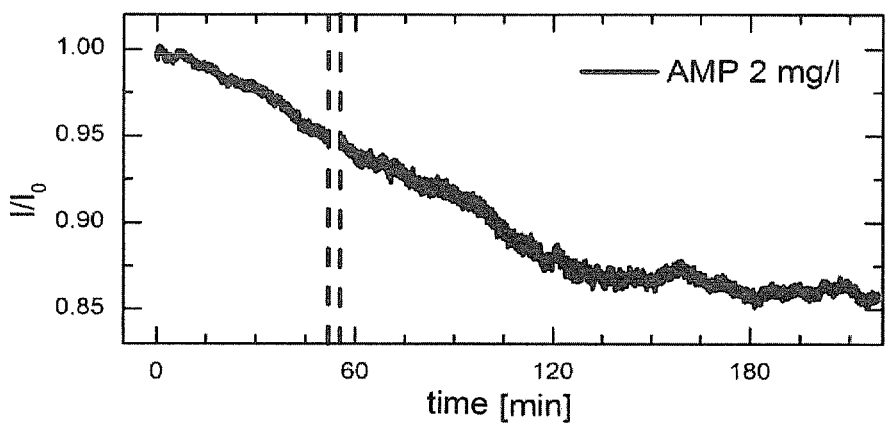
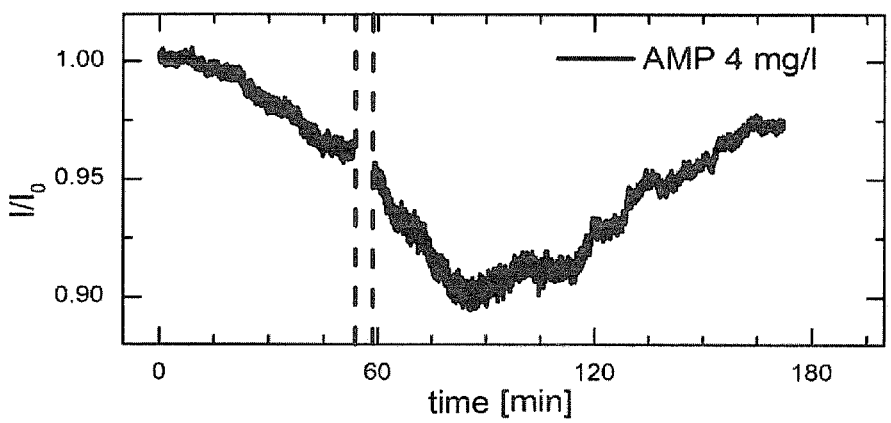

Fig. 19
d)
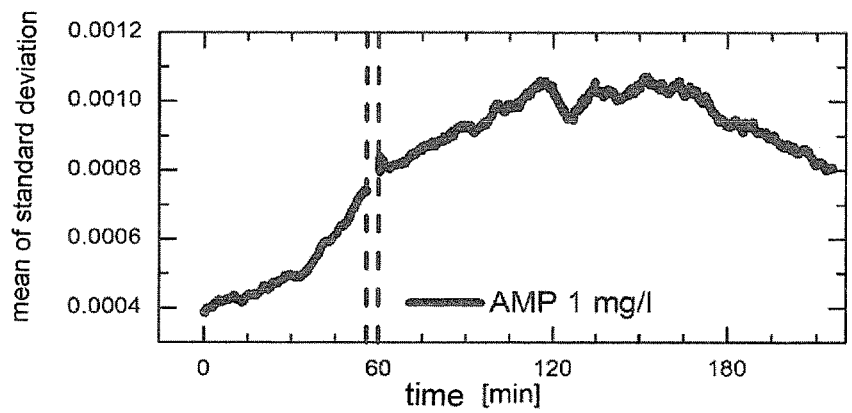
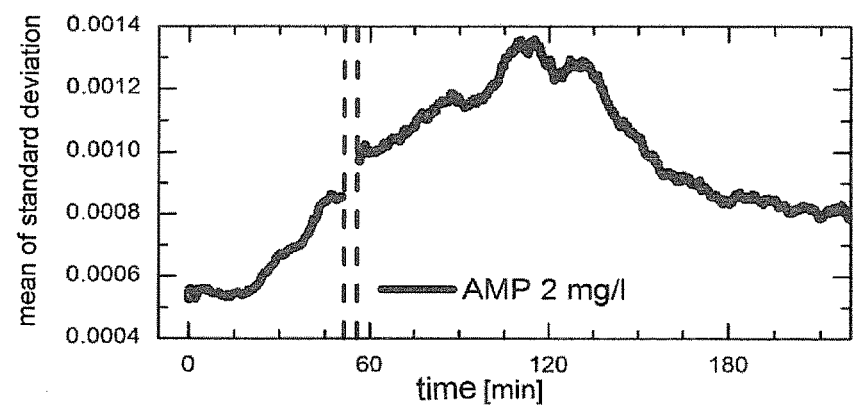
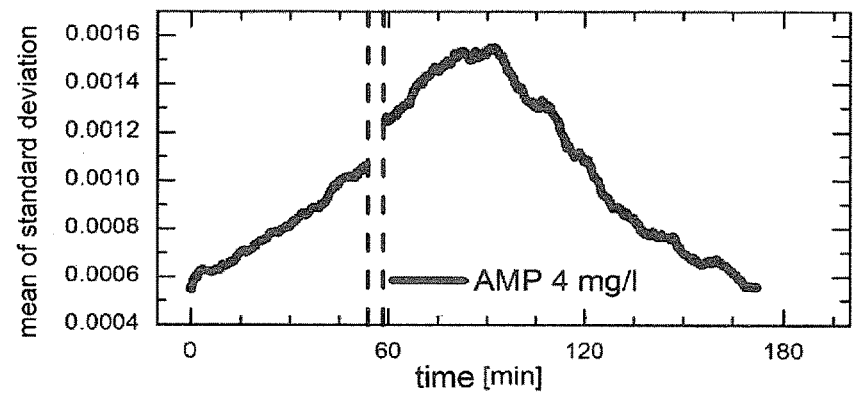

DEVICE AND METHOD FOR INVESTIGATING ONE OR A PLURALITY OF PHASE OBJECTS

CROSS-REFERENCE

The application claims the benefit of a German Patent Application No. 10 2013 112 415.1, filed on Nov. 12, 2013, the disclosure of which is incorporated herein in its entirety by reference.

FIELD OF THE INVENTION

The present invention is in the field of micro- or nanosensor technology. More precisely, the invention relates to a device and a method for investigating one or a plurality of phase objects, such as biological cells or minute animals, for example. The device and the method can be applied for example in cancer research, pharmaceutical research, immunology, inflammatory medicine, embryology and biotechnology.

BACKGROUND OF THE INVENTION AND RELATED PRIOR ART

Sensors are known from the prior art for measuring the force exerted by a biological cell. For example, DE 10 2011 050 493 A1 discloses a cell force sensor, which comprises a plurality of elastic elements, which are in each case fastened at the lower end thereof on a substrate and have an upper free end. The deflection of the elastic elements is ascertained on the basis of a diffraction image. However, a sensor of this type necessitates a structure with elastic elements, which can only be produced with increased outlay in an individual case.

Furthermore, a system for detecting the presence of an analyte is described in US 2005/0068543 A1. In this case, two grids are provided, arranged above one another in an offset manner. An identifying material for the analyte is arranged on one of the grids. The identifying material binds the analyte to it. When the analyte is bound to the grid, the optical depth of the modulation by the grid changes. However, this construction is not suitable for investigating a transient behaviour, such as for example a movement of biological cells, with small temporal resolution.

It is specifically the detection of the movement and (population) growth of biological cells that is desirable however for improved diagnostics, for example of cancer illnesses. Cancer illnesses are currently the second leading cause of death. By 2030, according to the American Cancer Society, the number of global cancer illnesses shall almost double again. The movability of cells, called cell motility in specialist circles, is an important indicator, among others, in wound healing, immune response, angiogenesis and in many illness-related changes, particularly metastasis in the case of cancer. Automatic measurement of cell motility is therefore of great importance for developing medical active agents.

Hitherto, methods were used for assessing cell motility, which are based on an image analysis of movement sequences of individual cells and determination of the average quadratic displacement of the cell per unit time. Cells are often investigated in 3D hydrogels, which constitute an artificial tissue matrix. These methods are cost- and time-intensive however, particularly if a larger number of cells should be observed for a statistical analysis.

BRIEF SUMMARY OF THE INVENTION

The invention is therefore based on the object of providing a method and a device for investigating phase objects, particularly a cell motility, with high temporal resolution, high flexibility and with low outlay, it being possible to investigate a large number of phase objects at the same time.

This object is achieved by a method according to claim 1 and a device according to claim 24. Advantageous developments are specified in the dependent claims.

In a first aspect, a method for investigating one or a plurality of phase objects is provided, whereby a grid made up of elements is used, which is illuminated with light of a light source, the coherence length of which is larger than the average spacing of adjacent elements of the grid. A diffraction image of the illuminating light scattered on the grid is generated, whereby the one or the plurality of phase objects are placed in the light path between the light source and the grid and/or in the light path of the illuminating light scattered on the grid. At least a part of the diffraction image is detected by an optical sensor directly or after interaction with further optical components and converted into a signal. The signal is analysed further in order to ascertain information relating to the one or plurality of phase objects therefrom.

Unlike in the described prior art, no chemical bonding between the phase object and the grid is required. As a result, the phase object can move substantially freely on the grid or above the grid, so that for example, the unhindered change, such as e.g. the unhindered movement thereof, can be ascertained. In particular it is possible using the described method to ascertain a level of coverage of the grid by the one or plurality of phase objects, a number of the phase objects, a change of the level of coverage or the number of the phase objects and/or a movement, a movability, a type, a shape, a surface change, a shape change, a refractive index, a volume change, a force exerted on the one or the plurality of phase objects, a force exerted by the one or the plurality of phase objects, a substance, to which the one or the plurality of phase objects are exposed, a physical stimulus, to which the one or the plurality of phase objects are exposed, a level of intermixing and/or a chemical composition of the one or the plurality of phase objects in real time in a temporal resolution not possible for normal optical microscopy technology and in the case of a large number of phase objects and/or a high density of phase objects in a short time. In particular, the method according to the invention enables a quantitative mobility test for biological, pharmaceutical and medical questions.

Furthermore, it is not necessary in the described method that the elements of the grid are flexible. Although in some embodiments, a grid with flexible elements is nonetheless used, a grid made from rigid elements can be used in other embodiments. A rigid grid is generally simpler to produce and to clean.

A phase object is generally understood to mean a three-dimensional object, which changes the phase relationship between the impinging and the reflected planar light wave between two grid elements. Generally, this requires that the phase object be transparent, at least to some extent, preferably completely, at a wavelength of the incident light. Unlike in the case of an amplitude object, it is not necessary in the case of a phase object, however, that the phase object contains pigments, which absorb a part of the incident light. A phase object generally has a refractive index which differs from that of a medium surrounding the phase object. Examples for phase objects are biological cells, such as e.g. cancer cells, particularly breast cancer cells, biological tissues, minute animals, fluids, such as for example liquid droplets, liquid films, gas layers, etc.

The described placement of the one or the plurality of phase objects in the light path ensures that a change at the phase object leads to a changed diffraction image. In many cases, the one phase object or the plurality of phase objects is/are arranged on the grid. The one or the plurality of phase objects can be placed on the grid directly and for example touch one or a plurality of elements of the grid. Alternatively, a transparent medium can be provided between the one or the plurality of phase objects and the elements of the grid and/or around the one or the plurality of phase objects, so that the one or the plurality of phase objects are not in direct contact with the elements of the grid. For example, a matrix can be arranged on the grid, as is described in detail below, and/or a protective layer can be arranged on or below the grid, as is likewise described below. The placement of the phase objects on the grid generally means that the phase objects are arranged at least to some extent in the light path of the light impinging onto the grid and/or diffracted by the grid.

In some embodiments, the light can run through a surrounding medium having a first refractive index before and/or after the impingement on the grid, whereby the one or the plurality of phase objects have a second refractive index, which is different from the first refractive index. It can be provided for example that the one phase object or the plurality of phase objects are located in a surrounding medium, such as for example air, water or an aqueous solution, which is arranged in the light path between the light source and the grid. For example, the surrounding medium can cover regions on the grid which are not covered by the one or the plurality of phase objects. Alternatively or additionally, the surrounding medium can be located on the side of the one or the plurality of phase objects facing away from the grid. The phase object(s) in this case has/have a different refractive index from the surrounding medium.

In order to protect the grid from chemical and physical influences, a transparent resistant protective layer can be applied on the grid, for example silicon oxide. Alternatively, a transparent substrate can be used, whereby the grid is located on the rear side of the substrate. Configurations of this type are explained in more detail below.

The phase relation and potentially also the light path of the incident light, which is diffracted at the grid, is changed by the presence of a phase object, as will be described further in detail below. For example, the incoming light, which runs through the surrounding medium, is refracted when entering into the phase object, before it reaches one of the grid elements. After reflection at the grid element, the light is refracted again during the transition out of the phase object into the surrounding medium. Thus, the path length of the light is lengthened by a path difference if a phase object is located above a grid element, as is quantified further below. Alternatively, the phase object can be placed in such a manner that it is only located in the light path between light source and grid or only in the light path between grid and optical detector. Due to the different path lengths, the phase relation of the light reflected at the grid element is also different. The light waves reflected by the grid elements are added in a phase-sensitive manner and result in terms of superposition in a diffraction image. Due to the change of the phase relation (a path difference) of the wave reflected at one of the grid elements in the presence of a phase object in the light path before or after the grid element, the diffraction image is therefore changed as a whole. Even if only one grid element or only a few grid elements are affected by a change of the phase object, this can nonetheless cause a substantial change of the diffraction image. Even in the case of an identical light path, e.g. in the case of perpendicular incidence of the light onto a planar phase object with a refractive index different from a surrounding medium, an optical path length difference of the light beam is achieved, owing to the dispersion relation of the light, which path difference in turn leads to a modulation of the diffraction image.

For example, it may be provided that the phase objects only cover one or a few of the grid elements. If the phase objects move and for example cover a further grid element or expose a previously covered grid element, the phase relation of the light diffracted at these grid elements changes, so that the entire diffraction image also changes. Indeed, even if no "new" grid elements are covered by the phase objects and also no previously covered grid elements are exposed in a time increment, the diffraction image can nonetheless be changed in that for example the shape or the refractive index of one or a plurality of the phase objects changes over one or a plurality of the grid elements. The optical path length of the emerging light and thus the phase relation thereof is also changed hereby, so that the diffraction image is also changed.

In some embodiments, the one phase object or the plurality of phase objects can cover all grid elements. For example, the phase object can be a fluid, which is located above the grid, such as a liquid for example. Using the method according to the invention, a surface movement of the liquid or a level of intermixing with another substance can then be ascertained for example, as in these cases, the height and/or shape of the phase object above the grid points or the refractive index of the phase object changes over time.

Using the method according to the invention, it is for example possible to investigate the activity of only one single phase object, for example a single cell, with high resolution. To this end, a single phase object can be arranged on the grid. Alternatively, in some embodiments, more than three, particularly more than 50 and preferably more than 100 phase objects, particularly biological cells, can be arranged on the grid. In this manner, a large population of phase objects can be investigated simultaneously, in order for example to ascertain a level of coverage of the grid by the phase objects, a number of the phase objects, a change of the level of coverage or of the number of phase objects, a movability, a shape change, a surface change or the like of the phase objects. In this manner, more statistically reliable results can be provided. As the investigation of the phase objects takes place by means of diffraction, i.e. in the Fourier space, no more effect is associated with the investigation of a large number of phase objects during the measurement. Rather, the spectrum of the movement caused by the totality of phase objects is hereby analysed, so that one obtains a significant signal about the motility and the state of the cytoskeleton, e.g. during the observation of cells as phase objects. The method according to the invention even allows the observation in real time, so that for example the effect of pharmaceuticals on the cells can be investigated in detail.

Even the size of the observation field can be adapted in a simple manner for a large number of phase objects, in that the grid is made to be sufficiently large and the light beam is widened if necessary by means of an optical system before the illumination of the grid.

The optical detector converts the detected diffraction image or the detected part of the diffraction image into a signal, in that it generates the signal on the basis of the detected diffraction image or the detected part of the diffraction image. The signal can for example represent a spatial distribution of the scattered illuminating light. Alternatively or additionally, the signal can specify the intensity of the scattered illuminating light in one or a plurality of parts of the diffraction image, for example at a principal or secondary maximum of the diffraction image, as will be explained below. The signal can for example be an electrical or an electromagnetic signal, for example a light signal or a radio signal. The optical detector can be set up to transmit the signal to the evaluation circuit via a wired or a wireless connection, such as an electrically conductive cable, a glass fibre cable or a radio connection for example. Alternatively or additionally, the optical detector can be set up to store the signal, for example in a non-volatile memory, such as e.g. a hard drive or a flash memory. The signal can be an analogue or a digital signal.

In a preferred embodiment, the optical detector detects a temporal sequence of diffraction images or parts of diffraction images and converts the same into a sequence of signals, and the sequence of signals is analyzed further, in order to ascertain the information relating to the one or the plurality of phase objects therefrom. Here, a temporal sequence is understood to mean a sequence of at least two temporally successively detected diffraction images or parts of diffraction images. Two diffraction images or parts of diffraction images are for example satisfactory in order to be able to determine a change of the one or the plurality of phase objects between the times at which the diffraction images or parts of diffraction images were taken. For better temporal resolution and for determining the reaction of the phase object to chemical, biological or physical effects, it is however generally advantageous if a temporal sequence of more than two diffraction images or parts of diffraction images is detected and converted into a sequence of signals, and the sequence of the signals is analyzed, as is explained in more detail hereinafter.

It is preferred that a temporal sequence of the diffraction image or the parts of diffraction images is detected in an identical spatial arrangement made up of the grid and the optical detector, so that the detected diffraction images or parts of the diffraction image can be compared with one another more easily. By means of the analysis of the sequence of the signals, changes of the one or the plurality of phase objects can be ascertained, such as e.g. a shape change, a surface change, a movement, etc.

The change to be ascertained can in this case be any change of the one or the plurality of phase objects, which changes a refractive index at least locally at a position in the light path from the light source to the grid and/or from the grid to the optical detector and/or changes a boundary surface between two optical media with different refractive indices. For example, the change can be a change within the phase object, such as a diffusion movement within a liquid for example. By means of the diffusion, the refractive index can change locally, as a result of which the phase relation of the exiting light and therefore the diffraction image can change. Due to the high sensitivity of the method according to the invention, diffusion or mixing procedures of this type can also be reliably observed in the case of very small quantities. Thus, material is saved, potentially hazardous waste is avoided and analysis costs are reduced. In other cases, the change can comprise e.g. a displacement of a membrane between two or more fluid reservoirs within the phase object, such as a membrane between cell constituents for example. A change of the surface, the volume, the alignment or the position of a phase object, can also be determined with the aid of the method according to the invention, as is explained in more detail hereinafter. Further examples of changes of phase objects, which can be detected using the method according to the invention, are described below.

In a preferred embodiment, at least two parts of the diffraction image are detected simultaneously by at least two mutually spatially separated optical detectors and converted into signals, whereby the signals are analyzed further, in order to ascertain the information relating to the one or the plurality of phase objects therefrom. The optical detectors can for example be arranged in such a manner that they detect different primary and/or secondary maxima of the diffraction image. In this embodiment, the signals can for example specify the intensities of the different primary and/or secondary maxima of the diffraction image.

In some embodiments, a part of the diffraction image, which for example comprises one or a plurality of primary maxima and/or a plurality of secondary maxima, is detected. A primary maximum of the diffraction image arises during detection in the reflection on the grid at points in space, at which the light beams reflected at the grid elements interfere positively. Upon detection in transmission through the grid, a primary maximum arises at points in space, at which the light beams running through between the grid elements positively interfere. Secondary maxima arise at points in space, at which only a few of these light beams positively interfere with one another. It can be provided that for example the intensity in a spatially fixed part of the diffraction image is detected, which e.g. comprises only one primary maximum.

In a preferred embodiment, at least the intensity of a primary maximum of the diffraction image is detected by the optical detector. To this end, a photodetector can for example be used as an optical detector. In addition, the intensities of further primary maxima and/or the intensities of secondary maxima can be detected e.g. using the same optical detector or one or a plurality of further optical detectors.

In a preferred embodiment, a transparent protective layer is arranged between the grid and the one or the plurality of phase objects, as has been described above. The protective layer can for example be used to achieve an improved compatibility between the phase object and the grid elements or also to protect the surface of the grid against chemical and mechanical influences. The layer can for example be only a few nanometers to a few micrometers thick. It should be transparent at the wavelength of the illuminating light. The protective layer can for example have a satisfactory mechanical stability, in order to function as a substrate for the grid.

In some embodiments, the one or the plurality of phase objects can be arranged in a container, which is arranged or can be arranged in the light path between the light source and the grid and/or in the light path of the illuminating light scattered on the grid, whereby the grid is located outside of the container. In this manner, a direct contact between the grid and the phase objects is prevented, so that the grid is protected and the phase objects are not influenced by the grid.

According to a preferred embodiment, the phase objects are biological cells or minute animals. This is the case in particular in the application in the medical field that has already been mentioned. In particular, the described method can be used to ascertain a cell activity, such as for example a cell motility, of biological cells.

In a preferred embodiment, a change of the one or the plurality of the phase objects is ascertained on the basis of the signal. In embodiments, in which the optical detector detects a temporal sequence of diffraction images or parts of diffraction images, the change of the one or the plurality of the phase objects can be ascertained in particular on the basis of the sequence of the signals.

According to a particularly preferred embodiment, the one or the plurality of phase objects can furthermore be exposed to a substance and/or a physical stimulus. In this manner, the effect of a medicine on cancer cells can for example be investigated in that e.g. a change of the cell activity is ascertained. Furthermore, this embodiment allows an investigation of the pharmacokinetics of medicines in real time. The physical stimulus can for example comprise an illumination with an excitation light, heating, an electromagnetic field, x-ray irradiation, a radioactive irradiation, a mechanical action with an object or the like.

According to a preferred embodiment, a surface and/or volume change of the one or the plurality of phase objects, a process within the one or the plurality of phase objects, a change of the density of the one or the plurality of phase objects and/or a movement of the one or the plurality of phase objects relatively to the grid is ascertained on the basis of the signal.

According to a preferred embodiment, a level of intermixing of at least two phase objects is ascertained on the basis of the signal. The phase objects can for example be arranged at the start of the investigation in various spatial regions and are mixed in the passage of time, for example owing to a diffusion or on the basis of a mechanical action, e.g. by stirring.

According to a preferred embodiment, a level of coverage of the grid by the one or the plurality of phase objects, a number of phase objects and/or a change of the level of the coverage or the number of phase objects is ascertained on the basis of the signal. In particular, a temporal change of the level of the coverage of the grid by the one or the plurality of phase objects or the number of phase objects can be ascertained on the basis of the signal. In embodiments, in which the phase objects are biological cells, a growth of a cell population can be ascertained for example. In a similar manner, a change, particularly a growth of a population of minute organisms, such as e.g. viruses, fungi or bacteria, which in alternative embodiments form the phase objects, can be ascertained. It can furthermore be provided that the phase objects are exposed to a substance and/or a physical stimulus, as is described at another place. As a result, the influence of the substance or the physical stimulus on the change of the population can be determined. For example, this enables a qualitative or quantitative characterization of the effectiveness of antibiotics, fungicides, etc.

According to a preferred embodiment, the grid is arranged on a substrate, particularly a rigid substrate. This enables a simpler grid production with standard lithography methods, as are used for example in the semiconductor industry. In addition, a higher mechanical stability is thereby ensured.

In other embodiments, it can however be provided that the substrate is flexible. In this manner, the diffraction image can be changed in a simple manner by bending the substrate. As a result, the substrate can be adjusted to various phase objects that are used.

According to a preferred embodiment, the diffraction image or the part of the diffraction image is detected at least to some extent in reflection on the grid. In this embodiment, the diffraction image arises due to the interference of the light beams reflected on the grid. To this end, the elements of the grid are constructed in a reflecting manner. Alternatively or additionally, the diffraction image or the part of the diffraction image can be detected at least to some extent in transmission through the grid. In these embodiments, the diffraction image arises due to the interference of the light beams passing through the grid between the grid elements. Provision can also be made to detect the diffraction image or a part thereof both in reflection and in transmission. To this end, a single optical detector or preferably a plurality of optical detectors can be used, for example one or a plurality of optical detectors for detection in reflection and one or a plurality of optical detectors for detection in transmission.

In a preferred embodiment, the grid is arranged on a transparent substrate, such as a glass substrate for example. On the one hand, this enables an optical investigation of the phase objects with other methods, in which illumination is carried out through the phase objects, for example using an optical transmission microscope. On the other hand, a transparent substrate also allows a detection of the diffraction image or a part thereof in transmission through the substrate alternatively or additionally to a detection of the diffraction image or a part thereof in reflection on the grid. In alternative embodiments, the substrate consists of silicon, silicon nitride or other phase-object-compatible solid bodies.

In some embodiments, the elements of the grid have a dimension in a range of 5 nm to 200 µm, particularly of 20 nm to 80 µm and preferably of 100 nm to 10 µm. Such dimensions are particularly suitable to reliably ascertain the movability of biological cells.

An intermediate space between adjacent grid elements can be empty or can be filled with a filler material.

In some embodiments, the grid has a period in a range of 10 nm to 100 µm, particularly of 40 nm to 50 µm and preferably of 200 nm to 20 µm. Such values for the grid period are advantageous for example for the determination of the cell motility. For example, the grid period can be chosen in such a manner that the phase object covers at least one grid element at least to some extent. To this end, it is advantageous if the grid period is smaller than a minimum dimension, particularly a minimum lateral dimension of the phase object, such as for example at most a fifth of the minimum dimension of the phase object.

According to a preferred embodiment, the elements of the grid are arranged periodically. However, it can be provided in other embodiments that the grid is quasi-periodic.

According to a preferred embodiment, the grid is a two-dimensional grid. This is preferred compared to other embodiments, in which the grid is a one-dimensional grid, as information relating to the phase object is ascertained in two dimensions.

In a preferred embodiment, the said temporal sequence comprises at least three, in particular at least 20 and preferably at least 100 temporally successively detected diffraction images or parts of diffraction images. In this case, a higher number of temporally successively detected diffraction images generally enables a higher accuracy during the ascertainment of the information with respect to the one or the plurality of phase objects.

In a preferred embodiment, a correlation, particularly a standard deviation or a Fourier analysis of the temporal sequence of the ascertained diffraction images or parts of the diffraction images is ascertained by means of processing of the sequence of the signals. Therefore, preferred information of the diffraction images is used for light intensity. As a result, a change of the phase objects between two adjacently recorded diffraction images or diffraction image parts can be determined in a simple manner. As a result, quantifiable information can be ascertained for example by means of the change of the one or the plurality of phase objects. Independently of whether a Fourier analysis of the temporal analysis is carried out, a Fourier analysis can be carried out on each individual diffraction image or diffraction image part of the temporal sequence.

By means of the method according to the invention, an investigation of phase objects is enabled with very high temporal resolution, so that for example a very high number of and also very fast changing processes of the phase objects can be investigated. A further advantage of a short temporal spacing between the detected diffraction images or parts of diffraction images is that a slow change of the illuminating light, such as e.g. a laser drift, does not significantly impair the results of the method. Generally, however, observations of changes of the phase objects are possible for example from the nanosecond range up to the minute range or hour and day range.

In some embodiments, the light is irradiated intermittently, e.g. in a pulsed manner. In this manner, the phase objects are not illuminated permanently, in order to reduce influencing of the phase object, such as for example a cell, by the light to the greatest extent possible.

According to a preferred embodiment, a characteristic of the one or the plurality of phase objects is ascertained on the basis of the signal, and the ascertained characteristic is compared with entries in a database and/or with a theoretical model, in order to ascertain the information relating to the one or the plurality of phase objects, particularly to ascertain a level of coverage of the grid by the one or the plurality of phase objects, a number of phase objects, a change of the level of coverage or the number of phase objects and/or a movement, a movability, a type, a shape, a surface change, a shape change, a refractive index, a density change, a volume change, a force exerted on the one or the plurality of phase objects, a force exerted by the one or the plurality of phase objects, a substance, to which the one or the plurality of phase objects are exposed, a physical stimulus, to which the one or the plurality of phase objects are exposed, a level of intermixing and/or a chemical composition of the one or the plurality of phase objects.

For example, it can be stored in the database that a certain characteristic ascertained on the basis of the signal or the sequence of signals is assigned to "healthy", "diseased" or "suspect" cells of a certain cell type. In this manner, a typing (cell diagnostics) can be carried out automatically, and warnings can be given if the phase objects change, e.g. move, in an unusual or unexpected manner. For example, an indication can be given, if a cell activity, such as for example a cell motility or cell growth is too high or too low, whereby the typing "too high" and "too low" is stored in the database—e.g. as a function of the cell type. The characteristic used for comparison with the entries of the database can for example comprise Fourier coefficients and/or intensities, which result during the Fourier analysis of the temporal sequence of detected diffraction images or detected parts of the diffraction images, which is carried out on the basis of the sequence of the signals, or a different characteristic ascertained from the sequence.

In some embodiments, a three-dimensional matrix is arranged on the grid, in or on which the one or the plurality of phase objects are arranged, in order to detect a three-dimensional change, e.g. a three-dimensional movement, movability or shape change of the one or the plurality of phase objects. For example, the grid can be coated with the matrix. The matrix can be transparent at least to some extent, in order to allow the light to pass through. The matrix can comprise a gel, for example a polymer gel or collagen. Thus, phase objects, particularly living cells can be investigated in or on various surroundings. In the case of the known elasticity of the matrix, this embodiment also makes it possible to ascertain a force exerted by the one or the plurality of phase objects.

In a further aspect, a device for investigating one or a plurality of phase objects is provided. The device comprises a receptacle for accommodating a sensor with a grid made up of elements. Furthermore, the device comprises a light source, which is or can be arranged in such a manner that it can illuminate a sensor arranged in or on the receptacle in such a manner that a diffraction image is created by the light of the light source scattered on the grid and one or a plurality of phase objects to be investigated are arranged in the light path between the light source and the grid and/or in the light path of the illuminating light scattered at the grid, and also an optical detector, which is set up to detect at least a part of the diffraction image directly or after interaction with further optical components and convert the same into a signal. Furthermore, the device comprises an evaluation circuit, which is coupled to the optical detector and receives the signal and which is designed to ascertain information relating to the one or the plurality of phase objects from the signal.

The evaluation circuit can comprise e.g. an analogue or digital circuit. For example, the evaluation circuit can comprise a processor, which is programmed to carry out the specified steps, stored on a non-volatile memory.

In a preferred embodiment, the optical detector comprises an image sensor and/or a photodetector. The optical detector can comprise e.g. one or a plurality of photodiodes and/or CCD cameras. The optical detector can convert the diffraction image or the part of the diffraction image into an electrical signal, such as for example a voltage or current signal or a pixel value, which is proportional to the intensity and supply the electrical signal to the evaluation circuit.

In a preferred embodiment, the optical detector is configured to detect a temporal sequence of diffraction images or parts of diffraction images and convert the same into a sequence of signals, whereby the evaluation circuit is designed to ascertain the information relating to the one or the plurality of phase objects from the sequence of the signals.

In a preferred embodiment, the temporal sequence comprises at least three, in particular at least 20 and preferably at least 100 temporally successively detected diffraction images or detected parts of diffraction images.

According to a preferred embodiment, the evaluation circuit is designed to carry out a correlation, particularly a Fourier analysis of the sequence of the detected diffraction images or the detected parts of the diffraction images by means of processing of the sequence of the signals.

In a preferred embodiment, the optical detector is arranged in order to detect at least the intensity and/or the position of a principal maximum of the diffraction image.

According to a preferred embodiment, the optical detector is a first optical detector, which is set up to detect a first part of the diffraction image and convert the same into a first signal, and the device comprises a second optical detector, which is spatially separated from the first optical detector and is set up to detect a second part of the diffraction image and convert the same into a second signal, whereby the evaluation circuit is further coupled to the second optical detector and receives the second signal and is designed to ascertain the information relating to the one or the plurality of phase objects from the first and the second signal.

In a preferred embodiment, the optical detector is arranged in order to detect the diffraction image or the part of the diffraction image at least to some extent in transmission through the grid and/or at least to some extent in reflection at the grid.

According to a preferred embodiment, the evaluation circuit is designed to ascertain a change of the one or the plurality of phase objects on the basis of the signal.

In a preferred embodiment, the evaluation circuit is designed to ascertain a surface and/or volume change of the one or the plurality of phase objects, a process within the one or the plurality of phase objects, a change of the density of the one or the plurality of phase objects and/or a movement of the one or the plurality of phase objects relatively to the grid on the basis of the signal.

According to a preferred embodiment, the evaluation circuit is designed to ascertain a level of intermixing of at least two phase objects on the basis of the signal.

According to a preferred embodiment, the evaluation circuit is designed to ascertain a level of coverage of the grid by the one or the plurality of phase objects, a number of the phase objects and/or a change of the level of the coverage or the number of phase objects on the basis of the signal.

In a preferred embodiment, the device further comprises a data memory with a database stored therein or can be coupled to the same, and the evaluation circuit is designed to ascertain a characteristic of the one or the plurality of phase objects on the basis of the signal, and to compare the ascertained characteristic with entries in the database, in order to ascertain the information relating to the one or the plurality of phase objects, particularly a level of coverage of the grid by the one or plurality of phase objects, a number of phase objects, a change of the level of coverage or the number of phase objects and/or a movement, a movability, a type, a shape, a surface change, a shape change, a refractive index, a density change, a volume change, a force exerted on the one or the plurality of phase objects, a force exerted by the one or the plurality of phase objects, a substance, to which the one or the plurality of phase objects are exposed, a physical stimulus, to which the one or the plurality of phase objects are exposed, a level of intermixing and/or a chemical composition of the one or the plurality of phase objects.

In some embodiments, the device can comprise a display or an interface for outputting the ascertained information relating to the one or the plurality of phase objects.

In a preferred embodiment, the optical component mentioned comprises a Fourier optical system, which is arranged in order to convert the diffraction image into a real image of an arrangement of the one or the plurality of phase objects. In this case, it is suggested to transform the Fraunhofer diffraction image by means of interaction with an optical system, for example a lens, from the Fourier space to the location or original space, in order to again obtain a "normal" image of the arrangement of the phase objects. The optical system can for example be a collimating lens, which is used as what is known as a Fourier optical system. The electrical field of the diffraction image located in the image-side focal plane in this case corresponds to the spatial Fourier transform of the electrical field in the object-side focal plane.

The use of such a Fourier optical system makes it possible to produce an enlarged real image without a microscope having to be used, and thus constitutes a cost-effective alternative for a conventional design with microscope. A further advantage of this development consists in the fact that a device which operates in an operating mode in Fourier space (for example in order to measure intensities of individual principal maxima) can be equipped rapidly and simply, in order to obtain a "real optical" image of the arrangement of the phase objects. In this manner, one obtains the advantages of both detection methods in one and the same device with minimal additional outlay on equipment with respect to a device based on diffraction pattern detection.

In a preferred embodiment, the device further contains a sensor with a grid made up of elements, which is accommodated in or on the receptacle.

In this case, it is particularly preferred that a protective layer is arranged on the grid of the sensor, in order to arrange the one or the plurality of phase objects thereon.

In a preferred embodiment, the device further comprises a container for accommodating the one or the plurality of phase objects, whereby the container is or can be arranged in the light path between the light source and the grid and/or in the light path of the illuminating light scattered at the grid, whereby the sensor with the grid accommodated in or on the receptacle is located outside of the container.

SHORT DESCRIPTION OF THE FIGURES

Figure 5:
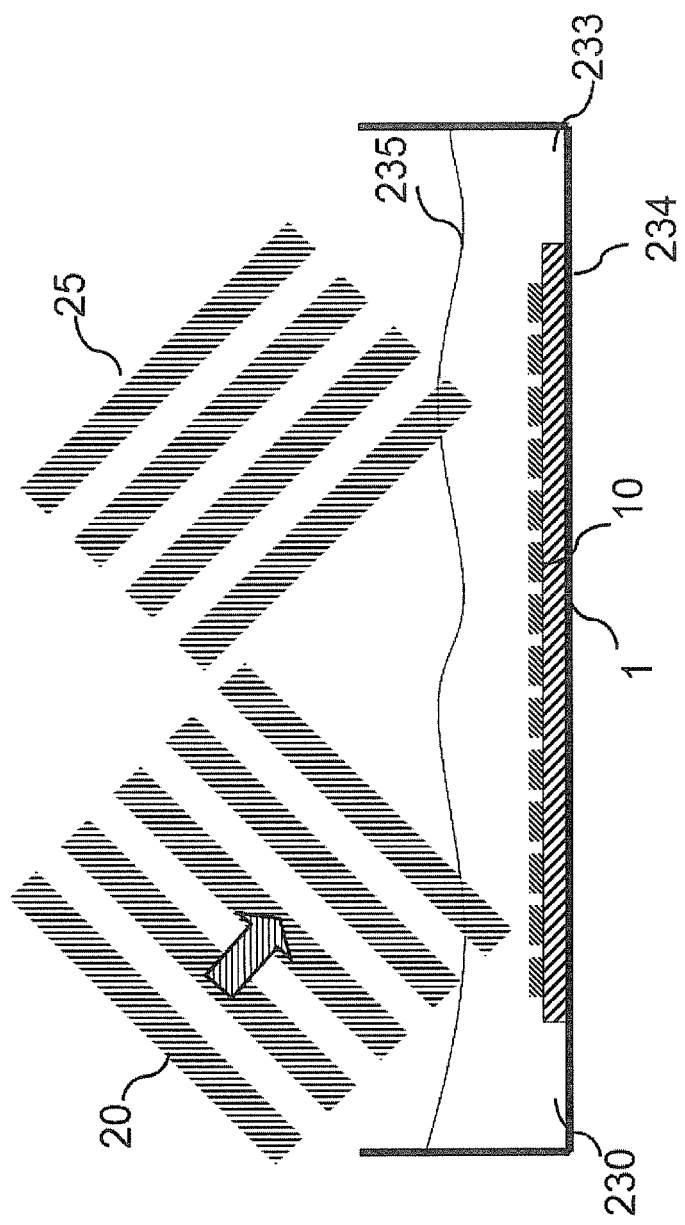
Figure 7:
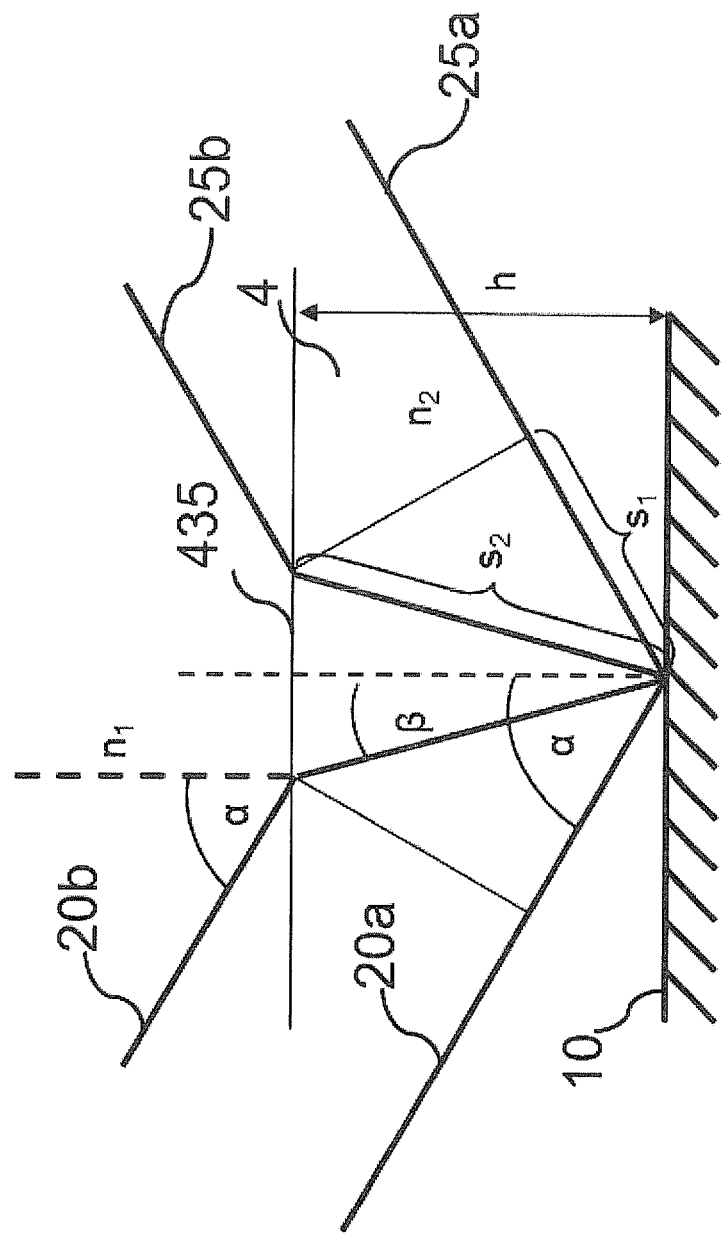
Figure 8:
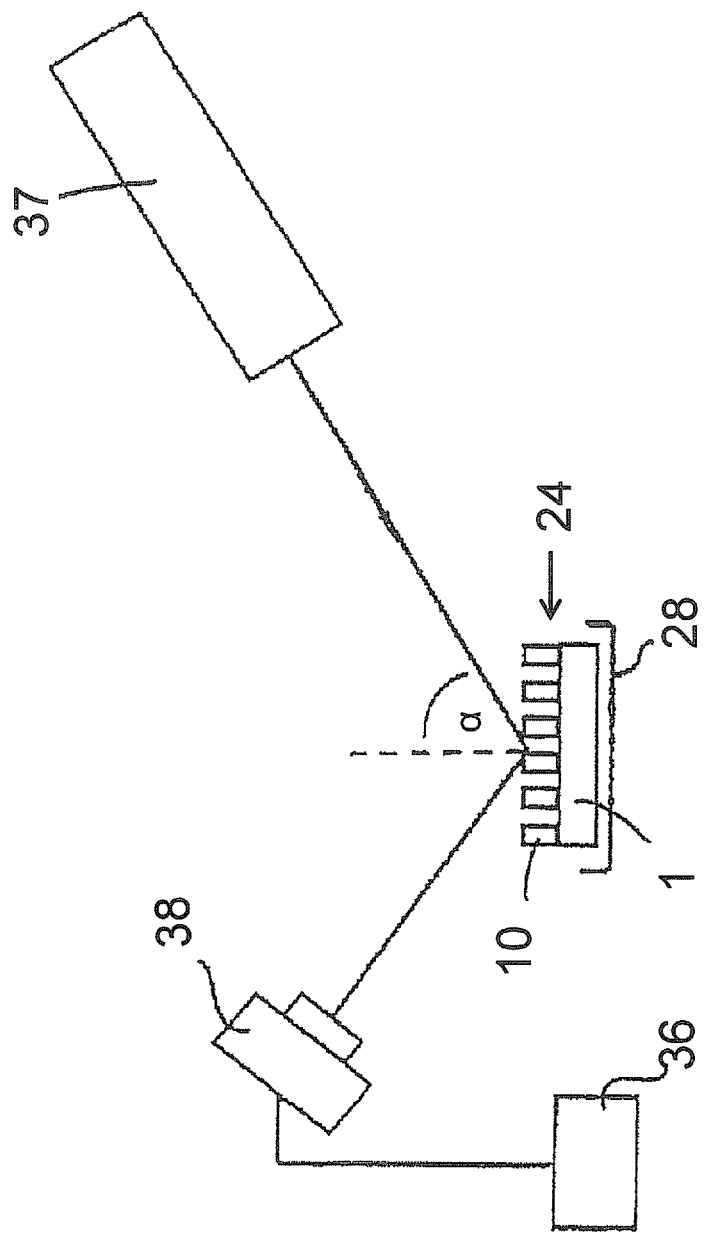
Figure 11A:
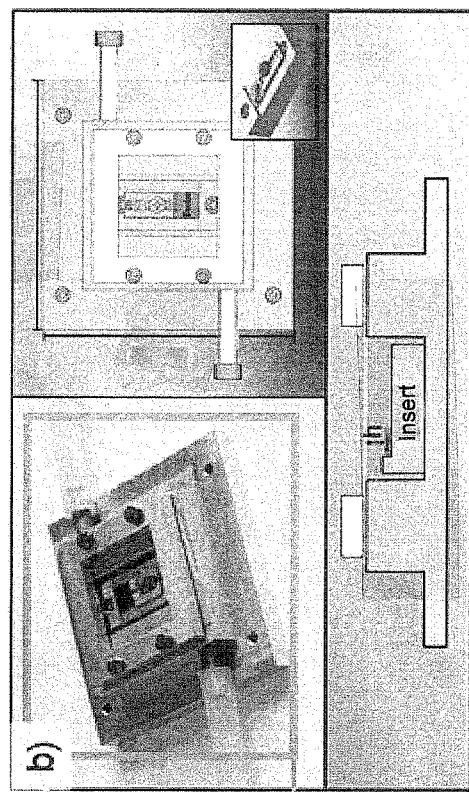
Figure 11B:
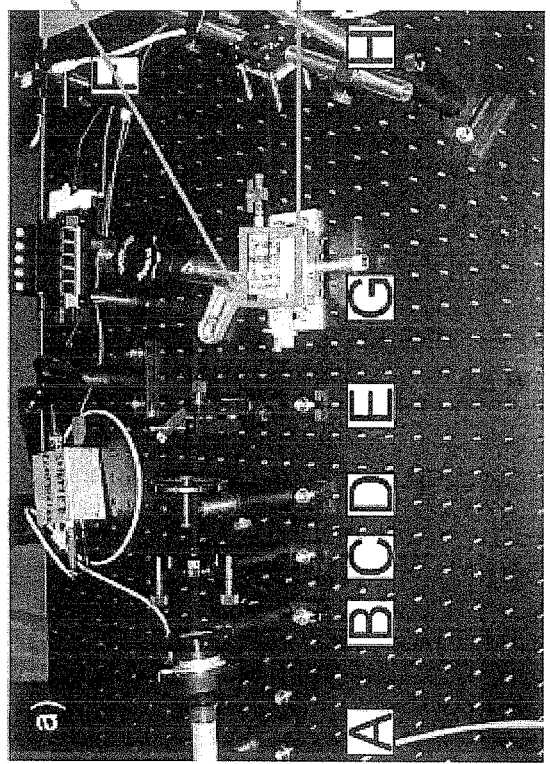
Figure 12:
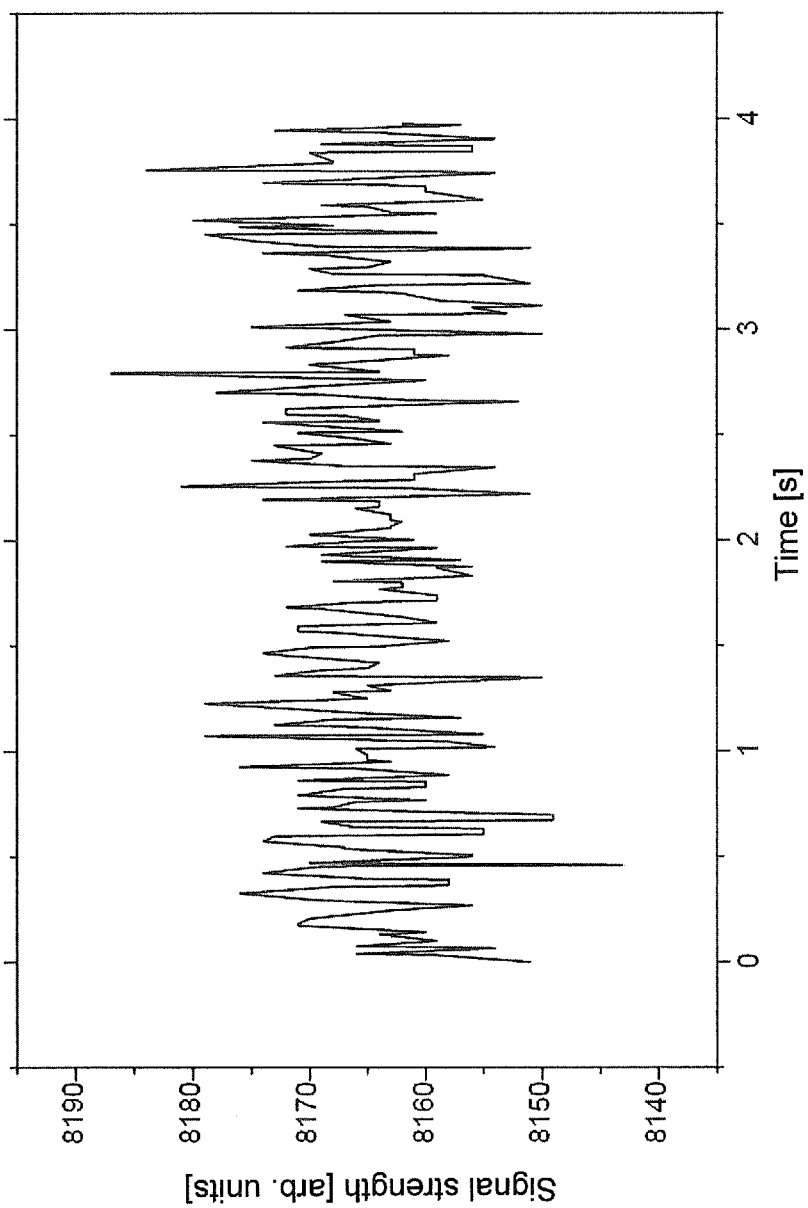
Figure 13:
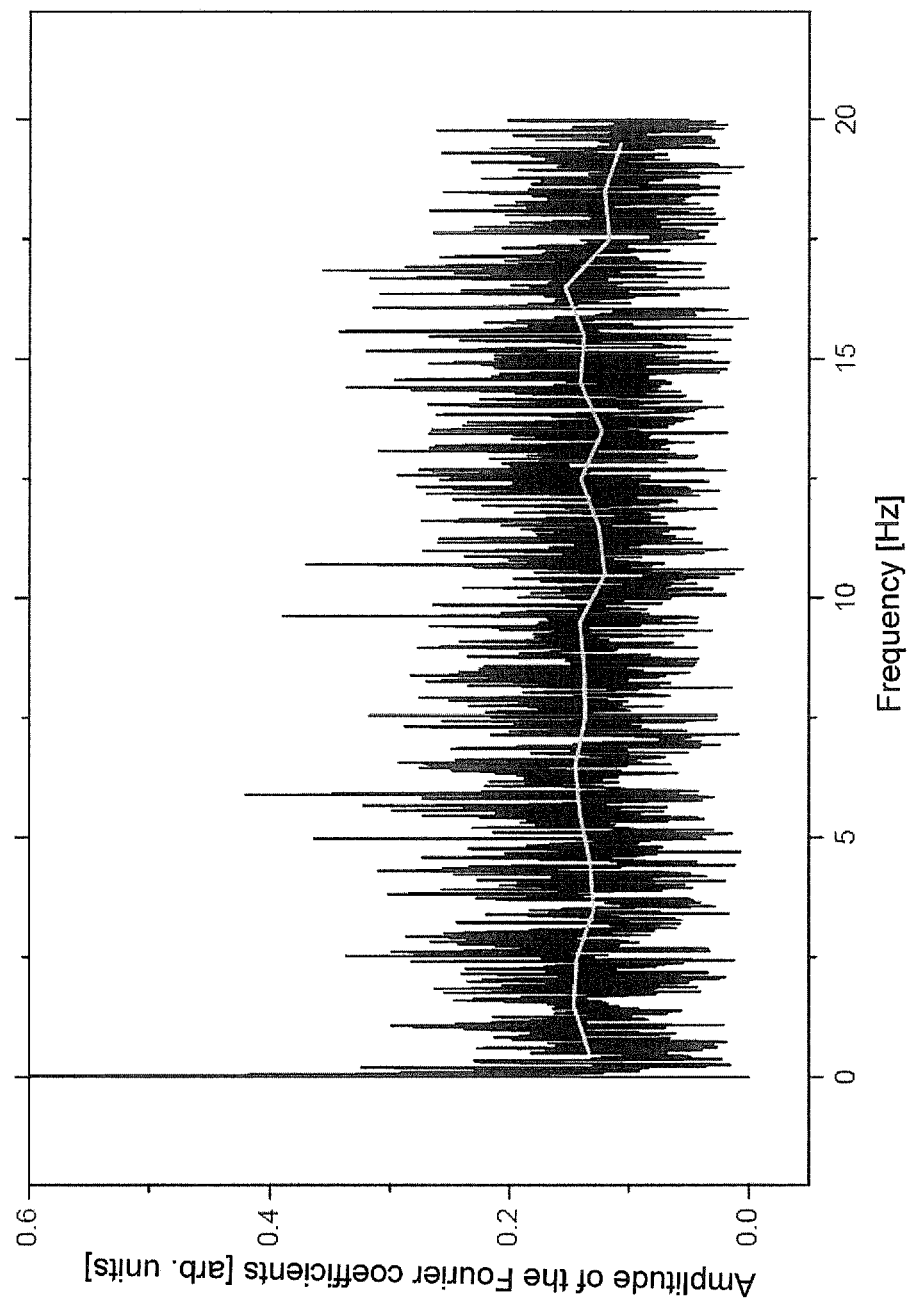
Figure 14:
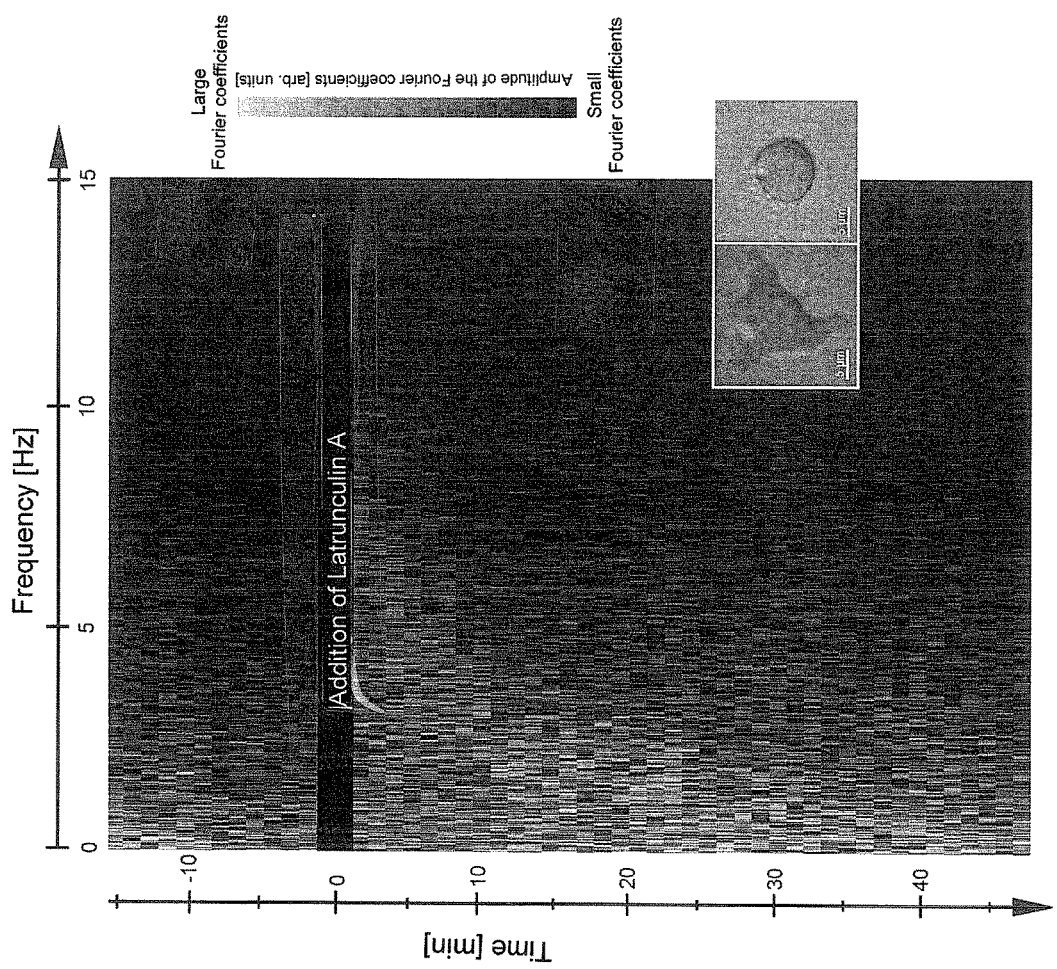
Figure 15B:
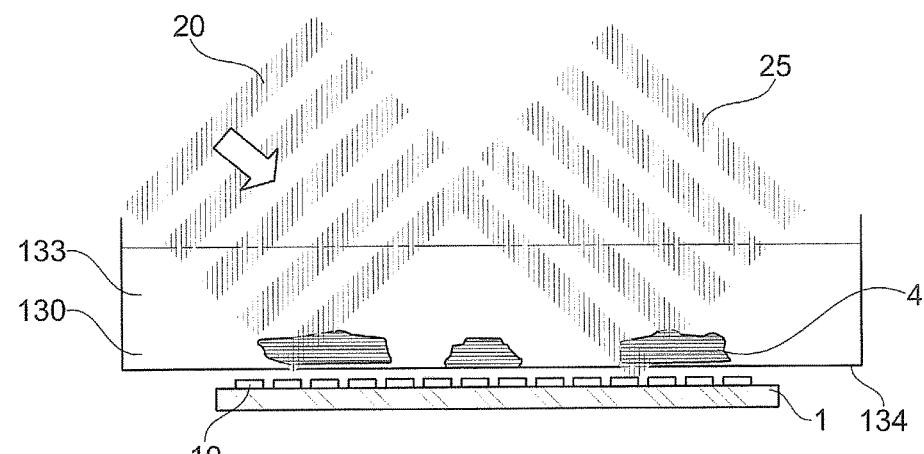
Figure 15A:
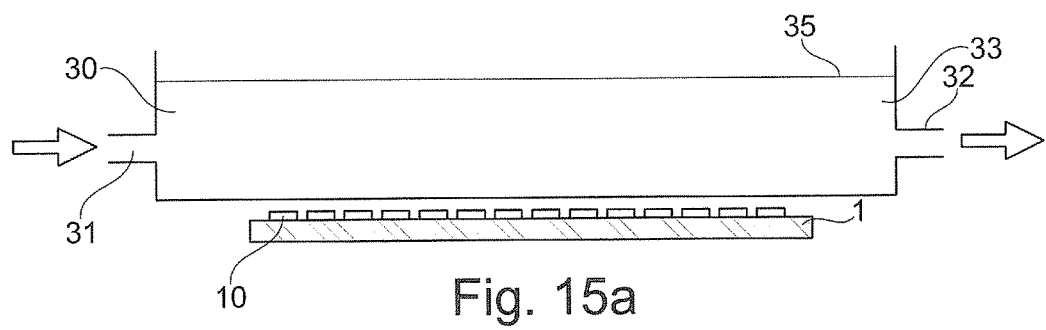
Figure 15C:
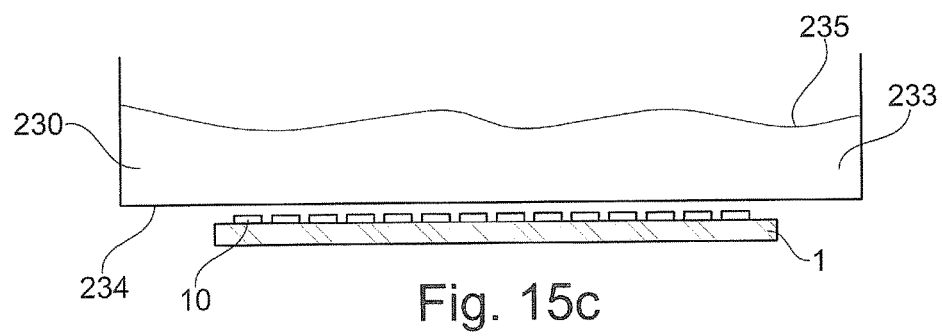
Figure 16:
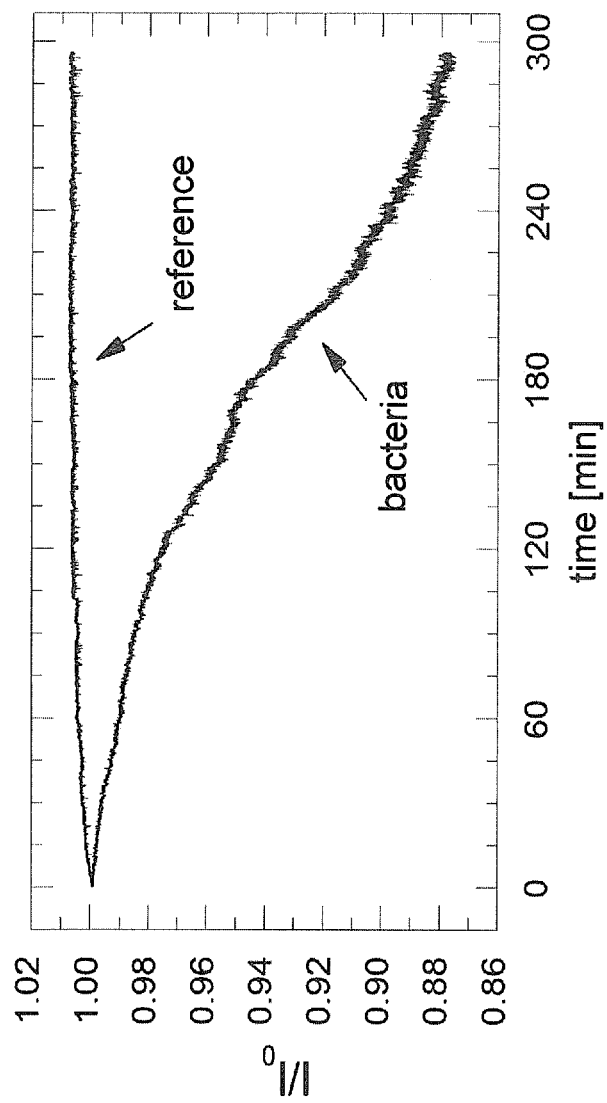
Figure 17:
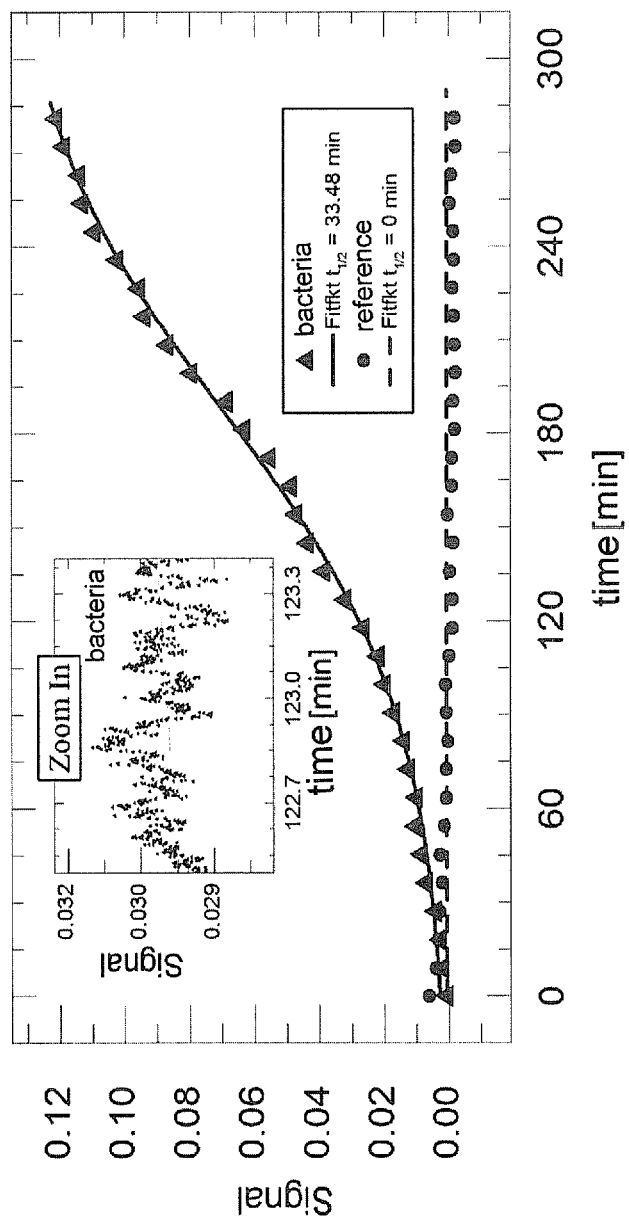
Figure 18:
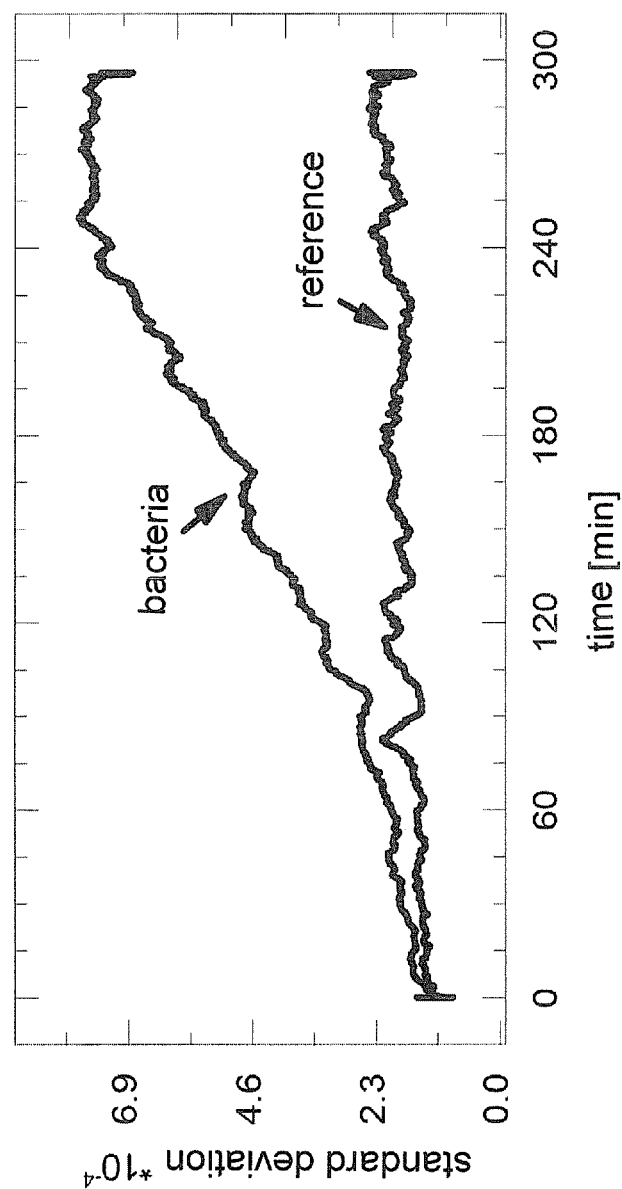

Further advantages and features of the invention result from the following description, in which the invention is explained on the basis of exemplary embodiments with reference to the attached drawings. In the figures FIG. 1 shows a grid, which is located on a substrate, in a profile view and a plan view, FIG. 2 shows a different grid, which is located on a substrate, in a profile view and a plan view, FIG. 3 shows a schematic illustration of the diffraction on a grid, which is located in a flow container, FIG. 4 shows a schematic illustration of the diffraction on a grid, with cells placed thereon, in a container, FIG. 5 shows a schematic illustration of the diffraction on a grid in a moved liquid, FIGS. 6a, b show a schematic illustration of the path of light in the case of diffraction at a grid without or with phase object, FIG. 7 shows a typical beam path in the case of reflection at a grid element and passage through a phase object, FIG. 8 shows a schematic illustration of a device according to the invention, FIG. 9a shows a bright-field microscope image in transmission of a grid, FIG. 9b shows a microscope image of the grid of FIG. 9a in reflection, FIG. 10a shows a bright-field microscope image in transmission of a grid with cells placed thereon, FIG. 10b shows a microscope image of the grid of FIG. 10a in reflection, FIG. 11a shows a photo of a device according to the invention, FIG. 11b shows a detailed view of a receptacle for a sensor, FIG. 12 shows a course of a detection signal in the time domain, FIG. 13 shows a course of the detected signal in the frequency domain, FIG. 14 shows a temporal course of the Fourier coefficients when an active substance is added, FIGS. 15a-c show embodiments similar to FIGS. 3-5, in which the grid is located outside of the container, FIG. 16 shows the normalized intensity of a diffraction maximum as a function of time with and without bacteria population, FIG. 17 shows measurement points of a signal that corresponds to the difference of the intensities without and with bacteria, as well as a corresponding fitting function, FIG. 18 shows the fluctuation of the intensity as a function of time, and FIG. 19 shows in column a) optical microscopy images of a sample at a time 0, in column b) optical microscope images at later points in time, in column c) the normalised intensity of the diffraction maximum as a function of time and in column d) the mean values of the standard deviation of the intensity as a function of time.

DESCRIPTION OF PREFERRED EMBODIMENTS

In the following, the method according to the invention is explained by way of example with reference to the attached drawings. In this case, the same reference numbers are used to designate similar elements.

FIG. 1 shows a grid made up of essentially cylindrical elements 10, which are arranged on a substrate 1. In the upper region of FIG. 1, a cross section through the grid with the substrate 1 can be seen, whilst a plan view onto the grid is illustrated in the lower region of FIG. 1. In the embodiment shown in FIG. 1, the grid is a two-dimensional periodic grid, wherein the grid periodicity is different in the two directions. However, it can be provided in other embodiments that the grid is a two-dimensional grid with the same grid periodicity in both directions.

FIG. 2 shows a different grid with elements 10', which can be used in the method according to the invention. The elements 10' are elongated elements that are arranged in parallel. Even if only two such elements 10' are illustrated in FIG. 2, the person skilled in the art will understand that further elements can be arranged parallel and for example with the same spacing in each case. The grid illustrated in FIG. 2 is therefore a one-dimensional grid.

The elements 10, 10' of the grids of FIGS. 1 and 2 can e.g. be made from gold, aluminium, titanium and/or silicon nitride, whilst the substrate 1 is for example made from silicon oxide, glass, silicon, silicon nitride or gallium arsenide. In other embodiments, the substrate can be flexible. In some embodiments, a further surface coating can be provided on the grid, such as a gel matrix for example. The grid and the substrate 1 together form a sensor, which can be used in a device according to the invention, as is explained further hereinafter. In addition, the grid can be provided with a protective layer or a matrix (not illustrated), as has already been described at the beginning. How information relating to one or a plurality of phase objects, such as e.g. changes of one or a plurality of phase objects can be ascertained using a sensor of this type is described in detail in the following.

FIG. 3 shows a receptacle, which is constructed as a flow container 30, for accommodating a sensor, such as e.g. the sensor of FIG. 1 or 2. The flow container 30 has an inlet 31 and an outlet 32, in order to allow a fluid 33, such as for example a liquid, to flow in or out through the flow container 30. In other embodiments, the fluid 33 can be a gas. A sensor, which has elements 10, which form a grid, and a substrate 1, is located on the base 34 of the flow container 30. The substrate 1 in this case lies on the base 34 of the flow container 30, whereby the grid is arranged on the side of the substrate 1 facing away from the base 34 of the container 30.

Incident light 20, which emanates for example from a coherent light source, particularly a laser, is irradiated onto the grid obliquely. In this case, the light 20 runs at an angle to the surface 35 of the fluid 33. Upon entry into the fluid 33, the light 20 is refracted at the surface 35 (not illustrated in detail in FIG. 3). After entry into the fluid 33, the light 20 impinges onto the grid, whereby it is reflected at the elements 10 of the grid. The diffracted light (schematically provided with the reference number 25 in FIG. 3) passes through the surface 35 back out of the fluid 33 and is diffracted anew upon passage through the surface 35.

The embodiment illustrated on the basis of FIG. 3 can be used for example in order to investigate the influence or the intermixing of various liquids within the flow container 30. For example, when the fluid flows into the container 30, the light path, the phase (owing to the dispersion relation) and/or the polarization between the surface 35 and the grid are changed, so that the phase relation of the exiting light 25 also changes. This influences the diffraction image, which can be detected at least to some extent using an optical detector. During the intermixing of liquids, a chemical reaction or during the dissolution of a solid in the fluid 33, the refractive index of the fluid 33 often changes. As a result, the angle of refraction of the light 20, 25 at the surface 35 and also the phase relation of the exiting light 25 likewise change. Thus, the diffraction image is also changed as a result of this. The conversion of a temporal sequence of diffraction images or parts of diffraction images of the light 25 into a sequence of signals and a subsequent evaluation of the sequence of signals therefore enables a determination of the point in time, from which an equilibrium has been reached. In particular, it is possible to determine at what time an equilibrium reaction is complete or at which time a liquid is homogeneously mixed. The fluid 33 therefore functions as phase object in this embodiment.

FIG. 4 illustrates a further embodiment of the method according to the invention. In this case, a receptacle is provided in the form of a container 130, which is filled with a fluid 133. A grid made up of elements 10, which is arranged on a substrate 1, is provided on the base 134 of the container 130. The substrate 1 is located on the base 134 of the container 130. In comparison with FIG. 3, a plurality of phase objects in the form of biological cells 4 are located on the grid of FIG. 4. By detecting temporally successive diffraction images of the exiting light 25, a change of the arrangement of the cells 4 on the grid and therefore a cell motility can be detected. The fluid 133 in the container 130 can for example be selected in such a manner that it has a refractive index, which differs substantially from the refractive index of the cells 4 on the grid. In this manner, a movement of the cells 4 on the grid effects a clearer change of the diffraction image.

FIG. 5 shows a receptacle for a sensor in the form of a container 230, which can be used in a further embodiment. A sensor is located in the container 230, which is constructed as a sample chamber as in the FIGS. 3 and 4, which sensor comprises a grid made up of elements 10, which is arranged on a substrate 1, and also a fluid 233, which covers the grid. The substrate 1 lies on the base 234 of the container 230. In the scenario shown in FIG. 5, the surface 235 moves. Due to the temporal change of the surface, the height and the surface curvature of the fluid 233 above the grid elements 10 and thus the distance, which the incident light 20 must cover through the fluid 233 before it reaches the grid elements 10, also change locally. Thus, the phase relation of the exiting light 25 also changes. Due to a detection of a temporal sequence of the diffraction images or diffraction image parts of the exiting light 25, a movement of the surface 235 can therefore be detected and visualized for example. In this embodiment, the fluid 233 itself is used as a phase object. As the movement of the surface can for example be caused by vibration, the device according to the invention therefore provides a vibration sensor. The same can for example be used in the context of a burglar alarm, a seismograph or the like.

FIGS. 6a and 6b schematically illustrate the change of the phase relation of the exiting light 25 as a result of a phase object being present on the grid. FIG. 6a shows the case that incoming light 20a-d is only reflected at elements 10a-d of the grid, without running through phase objects. The reflected light 25a-d in this case forms a uniform diffraction image.

FIG. 6b then shows the case that a phase object, such as for example a cell 4 that is schematically drawn, is located on the grid to some extent. In the scenario shown in FIG. 6b, the cell 4 covers two grid elements 10b,c. With regard to the reflection at the grid elements 10a,d, which are not covered by the cell 4, nothing changes compared to FIG. 6a. With regard to the grid elements 10b,c, however, which are located beneath the cell 4, the incident light 20 must initially run for a distance $s_2$ through the material of the cell 4, before it impinges onto the grid elements 10b,c. Upon entry into the cell 4, the light 20b,c in this case experiences a refraction, which is determined by the refractive index $n_1$ of the surrounding medium and the refractive index $n_2$ of the cell 4. Also, after the reflection at the grid points 10b,c, the reflected light 25b,c initially runs through the cell 4 before it is diffracted anew at the surface thereof.

When comparing the path length of the exiting light 25a,b at the grid elements 10a and 10b, one can see that due to the presence of the cell 4 above the grid element 10b, the beam path of the incident and reflected light is changed. Due to the path to the grid element 10b that is longer by $s_2-s_1$, above which grid element the cell 4 is located, compared to the grid elements 10a in FIG. 6b or also to the grid element 10b in FIG. 6a (i.e. without a phase object), the phase relation of the reflected light 25b also shifts. This phase change influences the diffraction image, which is formed by the exiting light beams 25a-d. Due to the detection of the diffraction image or a part thereof, a position of the cell 4 on the grid can therefore be ascertained. Furthermore, the detection of a temporal sequence of diffraction images also enables a determination of a change, e.g. a movement of the cell.

FIG. 7 illustrates the mathematical relationship between the path difference of the reflected light beam 25b at a grid element 10, when a phase object 4 is located on the grid element 10. Upon entry into the phase object 4, the incoming light 20b is initially diffracted at the surface 435 of the phase object 4. After reflection at the grid element 10, the exiting light 25b again passes through the surface 435 of the phase object 4 and is there refracted again. For a height h of the phase object 4, an angle of incidence α of the incoming light 20b and an angle θ between the light beam and the grid normal in accordance with the refraction at the surface 435 of the phase object 4, the following results:

$$\cos(\beta)=h/s_2 \tag{1}$$

$$\Rightarrow s_2=h/\cos(\beta) \tag{1a}$$

$$\cos(\alpha-\beta)=s_1/s_2 \tag{2}$$

$$\Rightarrow s_1=\cos(\alpha-\beta)\cdot s_2 \tag{2a}$$

The path difference of the light, which results due to the presence of the phase object 4 on the grid element 10, is therefore:

$$\Delta g=2\cdot\Delta s=2\cdot(s_2-s_1)=2\cdot h/\cos(\beta)(1-\cos(\alpha-\beta)) \tag{3}$$

The angle of incidence α of the incoming light is in this case predetermined by the relative arrangement of the light source and the grid. If the light source, for example a laser, is securely mounted, and the receptacle for the sensor having the substrate and the grid predetermines an unambiguous angular orientation of the grid face relatively to the light source, the angle α is therefore also fixedly predetermined.

The angle β further depends, in accordance with Snell's law of refraction, on the angle of incidence α and also on the relationship of the refractive index of the phase object $n_2$ and the surrounding medium $n_1$. This relationship may be constant for example during the measurement of the motility of biological cells. Deviations can result however, for example when an active substance is added to the surrounding medium during the measurement, so that $n_1$ changes.

Furthermore, the height h of the phase object 4 influences the path difference and therefore the diffraction image of the exiting light. A change of the height h of the phase object above the grid element 10 however indicates a movement of the phase object 4, which should be detected with the aid of the diffraction image. If, e.g. for a current diffraction image, a higher height h above a grid element is present than for a preceding diffraction image, this may mean that the phase object 4 has just moved above the corresponding grid element.

Furthermore, the refractive indices of the phase objects and the surrounding medium have a decisive influence on the resulting diffraction image. A change of the refractive index of a phase object for example also changes the optical path length of the light and therefore effects a change of the phase relation without changing the external shape and without a movement of the phase object. Furthermore, the diffraction image is also influenced by the surface curvature of the phase object. The angle of incidence of the light is changed relatively to the surface by means of a local change of the surface curvature, so that the angle of refraction at the surface and therefore the course of the light within the phase object also changes. A change of the surface curvature in the region, in which the light emerges from the phase object, also changes the diffraction image.

In many applications, it may however be the case that one is not at all interested in the concrete behavior of individual phase objects, e.g. individual cells, but rather on the statistical behavior of a multiplicity of phase objects. One example for this is the investigation of how the addition of a certain active substance, for example a medicine, affects the movability of the cells. In this case, one would therefore not be interested in the current position of a phase object 4, but rather in an average value of a change of the movement of a plurality of phase objects for example.

To this end, instead of the conventional direct optical microscope image, a diffraction image of the grid with the phase objects placed thereon is created and detected according to the invention. A device is used for this purpose, as is shown schematically in accordance with an embodiment in FIG. 8. The device comprises a receptacle 28, which is suitable for accommodating the sensor 24. The receptacle 28 can be any section or any component, on or in which the sensor 24 can be arranged. For example, the receptacle 28 can be a container or a sample chamber, as has been described above. The sensor 24 further comprises at least one substrate 1 and at least one grid made up of elements 10 arranged thereon.

Furthermore, the device comprises a light source 37, which is a laser for example. The light source 37 must have a coherence length which at least exceeds an average spacing of adjacent grid elements 10, in order to create a meaningful diffraction image. However, in the case of the microscopic or nanoscopic dimensions of the grid, this is not a particularly strict requirement for the light source 37, so that the use of a laser as light source 37 is not obligatory, rather other light sources may also be considered. As illustrated in FIG. 8, the light source 37 is arranged at an angle α in relation to a plane defined by the grid.

Furthermore, the device comprises an optical sensor 38 which is suitable for receiving and detecting at least a part of the diffraction image. The optical detector 38 can for example be formed by a CCD camera or a photodiode. The optical detector 38, the receptacle 28 and the light source 37 can be positioned in such a manner that the optical detector 38 detects selected principal maxima and/or secondary maxima of the diffraction image and permits the intensity measurement thereof. The optical detector 38 converts the diffraction image detected by it or the part of the diffraction image detected by it into a signal, for example an electrical signal. In addition, the device contains an evaluation circuit 36 which is coupled to the optical detector 38 and which receives the signal and is designed to ascertain the information relating to the one or the plurality of phase objects from the signal. In particular, the evaluation circuit 36 can analyse a sequence of signals, which were generated by the optical detector based on a temporal sequence of successive diffraction images or successive parts of diffraction images, which were detected by the optical detector 38, in order to ascertain information therefrom relating to the one or the plurality of phase objects, which are arranged on the grid of the sensor 24. For example, a density of phase objects, e.g. a cell density, can be ascertained. Alternatively or additionally, a level of the coverage of the grid by the one or the plurality of phase objects, a number of the phase objects, a change of the level of the coverage or the number of the phase objects and/or a movement, a movability, a type, a shape, a surface change, a shape change, a refractive index, a level of intermixing and/or a chemical composition of the one or the plurality of phase objects can be ascertained.

Optionally, the device can contain a data memory (not shown), which is coupled to the evaluation circuit 36. The data memory can store a database. The evaluation circuit can be set up to determine a characteristic of the one or the plurality of phase objects on the basis of the signal, and to compare the ascertained characteristic with entries in the database, in order to ascertain the information relating to the one or the plurality of phase objects. The information ascertained in this manner can for example relate to a type of one or a plurality of cells, a cell density, a cell activity, particularly a cell movement and/or a cell surface change, a refractive index, a liquid movement, an active substance, a chemical reaction or the like.

Although a detection of the diffraction is shown in reflection in FIG. 8, the diffraction image or a part thereof can additionally or alternatively be detected in transmission in alternative embodiments by placing the optical detector or a region thereof such as to detect light running through the substrate 1. In some embodiments, a Fourier optical system (not shown) can alternatively or additionally be provided in the light path between the sensor 24 and the optical detector 38.

The distance between the optical detector 38 and the grid can for example lie in the single- to double-digit centimeter range. Compared with the order of magnitude and the spacings of the grid elements 10, this is hence a large distance, so that in the region of the optical detector 38, the diffraction image corresponds to the far field or the Fraunhofer diffraction pattern, which for its part corresponds to the two-dimensional Fourier transform of the field distribution directly after the diffraction structure. Even in a miniaturized embodiment, this would still apply with good accuracy if the distance between the grid and the optical detector 38 were to lie only in the double-digit μm range.

FIGS. 9a, b and 10a, b each show microscope images, whereby the FIGS. 9a, b show a grid without phase objects and FIGS. 10a, b show a grid with a cell arranged thereon. FIGS. 9a and 10a each show a transmission microscope image in the bright field. Whilst no structures can be recognized in FIG. 9a, FIG. 10a clearly shows the outlines of a cell.

FIGS. 9b and 10b each show a monochromatic microscope image in reflection, i.e. after diffraction at the grid. The regular grid structure of an (in this case) one-dimensional grid without disruptions of the regularity can be seen in FIG. 9b. By comparison, FIG. 10b shows a few irregularities of the bar-like structures, which correspond especially to the outline of the cell, as can also be seen in FIG. 10a. Owing to the clear deformation of the bars, the position of the cell in FIG. 10b can be recognized clearly.

FIG. 11a shows a device for investigating one or a plurality of phase objects according to an embodiment. In this case a light source in the form of a diode laser A is provided. A shutter B, a polarization filter C, a filter wheel D and a beam splitter E are provided in the light path downstream of the diode laser A. Furthermore, the device comprises two optical detectors F, H. By providing two optical detectors F, H, the diffraction image that appears can be compared with a diffraction image after diffraction at a regular grid without phase object for example. Furthermore, the device illustrated in FIG. 11a also comprises a sample holder G, which can for example comprise a receptacle for a sensor.

FIG. 11b shows the sample holder G of FIG. 11a in detail. In FIG. 11b, a three-dimensional view is shown top left, a plan view is shown top right, and a cross section of the sample holder G is shown at the bottom. As can be seen top left and top right in FIG. 11b, the sample holder comprises an inlet and an outlet, which are connected to tubes in each case. A surrounding medium or an active substance can be introduced into the receptacle, which is formed by the sample chamber. A sensor with a grid, which is arranged on a substrate, is located within the sample chamber. The lower region of FIG. 11b shows a cross section through the sample holder G. In this case an insert is illustrated, which comprises the grid and the substrate. Furthermore, biological cells are located on the grid, where the reaction of the cells to the active substances is to be investigated. In particular, in the illustrated case is to be investigated how the motility of the cells changes due to the addition of the active substance.

FIG. 12 shows the temporal course of the signal strength detected at the optical detector, the intensity of the first order Bragg reflexes in the same. By comparison, FIG. 13 shows a Fourier analysis of the temporal signal, which is illustrated in FIG. 12.

FIG. 14 shows a temporal course of the Fourier coefficients. In this case, the time axis runs from top to bottom and the frequency axis runs from left to right. At time t=0, the active substance, Latruncalin A, is added to the medium located in the sample chamber. In FIG. 14, at this time a rise in the Fourier coefficients, which subside again with increasing exposure time, can clearly be seen as a reaction to this. The inserted image bottom right in FIG. 14 shows a light-microscope image of a Dictyostelium discoideum cell before (left) and after (right) the addition of Latrunculin A, which is arranged on the grid of the sensor.

FIGS. 15a-c show embodiments which are similar to the embodiments shown in FIGS. 3-5, in which the grid is located outside of the container however. As a result, a direct contact between the phase objects and the grid elements is avoided. On the one hand, the grid elements are hereby protected from corrosion for example. On the other hand, it is further prevented that the phase objects, which are biological cells for example, are influenced by the material of the grid elements. As the arrangements in FIGS. 15a-c otherwise correspond to those of FIGS. 3-5, reference is made to the above detailed description, in order to avoid repetitions. For easier comparison, the same reference numbers have been used in FIGS. 15a-c as in FIGS. 3-5. Whilst in the embodiments of FIGS. 15a-c, the grid is arranged below the base of the container in each case, it is to be noted that in other embodiments, the grid can also be arranged laterally next to the container or thereabove, depending on the arrangement of the light source and alignment of the incident illuminating light.

The embodiment shown in FIG. 15a-c, in which the phase objects are arranged in a container that is separate from the grid, has a number of practical advantages. One advantage is that this structure allows for a variable distance between the sample container and the grid. If the vertical distance between the sample container and the grid as shown in FIG. 15 is large enough, it becomes possible that the light passes the sample only once before it is detected at the detector. Further, it is possible to keep the light source, the grid and the detector in a precisely adjusted position and to then move different sample containers into the light path, without requiring new or additional adjustments. Exchanging the sample container may be carried out partially or completely automatically, whereby the yields can be increased.

Modifications of the described embodiments are possible. For example, alternatively or additionally to the diffraction image, which is formed by the light beams reflected at the grid elements, the diffraction image, which is formed by light beams passing through between the grid elements, can be detected. In some embodiments, a plurality of optical detectors are provided, in order to detect different parts of the diffraction image.

FIG. 16 shows the normalized intensity of a diffraction maximum as a function of time. A reference curve shows the normalized intensity in a maximum of the diffraction image of the light that is diffracted by the grid in absence of bacteria. A further curve shows the normalized intensity in a case where the bacteria in a nutrition solution are present as phase objects in the light path. In FIG. 16, it can be seen that the intensity of the diffraction maximum decreases with time for the bacteria sample. This decrease is due to an increasing division of the bacteria, i.e. a continuous increase in the bacteria population or, in other words, an increase in the number of phase objects which increasingly disturb the constructive interference in the diffraction maximum and thereby lead to a decrease in the intensity. In FIG. 16, it can be further observed that with increasing time, the intensity increasingly fluctuates, which can be attributed to the activity of the cells.

FIG. 17 shows measurement points of a signal, which corresponds to the difference between the reference intensity and the intensity in presence of bacteria. Only separate selected measurement points are shown, to allow that at the same time a solid line of a fit function curve is displayed, which represents a certain cell division rate, in the present case 33.48 min. Further shown in FIG. 17 is an exemplary enlarged section of the course of the measurement signals, in which the fluctuations of the signal can be clearly seen. By fitting a growth curve, which includes the division rate as a parameter, the division rate of the bacteria can be discerned from the signal.

FIG. 18 shows the fluctuation intensity as the function of time, which fluctuation is represented by the standard deviation of the signals with regard to a smooth fitting curve. It can be seen from FIG. 18 that the standard deviation increases with time. This standard deviation represents fluctuations of the signals on a short time scale which in turn are a measure for the activity of the bacteria, which will be explained in more detail with reference to FIG. 19 below.

FIG. 19 shows in col. a) optical microscopy images of a sample at a time 0 with a given initial bacteria population. Column b) shows optical microscopy images at later points in time, namely after 215 min. in the first row, after 208 min. in the second row and after 172 min. in the third row. Column c) shows the normalized intensity as a function of time and column d) the mean value of the standard deviation as a function of time.

The first row of FIG. 19 shows a case in which the bacteria have been treated after 60 min. of growth with an antibiotic AMP having a concentration of 1 mg/l. It can be seen that after the treatment with the antibiotic, the normalized intensity decreases, which indicates a further growth of the bacteria population. At the same time, in row 1, column d) it can be seen that, unlike the situation of FIG. 18, the standard deviation reaches a plateau at 120 min. and decreases thereafter, which suggests that the bacteria cells die.

The second row shows a similar situation, except that a double dose of 2 mg/l AMP is applied. It can be seen that the decrease in the normalized intensity flattens at 120 min., i.e. that the cellular (population) growth is significantly slowed down in this time region. At the same time, it can be seen in row 2, col. d) that at 120 min. the standard deviation decreases significantly, which is again indicative of cell death.

The third row shows a similar characteristic, except that at 60 min. a yet higher dose of antibiotic AMP of 4 mg/l is applied. In the third row, column d) one can again see a rapid decrease in the standard deviation, which is even more pronounced than in the second row, as was to be expected in view of the double dose of the antibiotic. Further it can be seen in row 3, column c) that the intensity starts increasing again after 90 min. This indicates that the cells not only die as a result of the high antibiotic concentration, but at least partly dissolve, a fact that can also be seen from the comparison of the microscopic images in column b). Due to their disintegration, the bacteria lose their function as "phase objects" such that the intensity in the diffraction maximum increases again.

REFERENCE LIST

1 Substrate
10, 10', 10a-d Grid element
20, 20a-d Incoming light
25, 25a-d Exiting light
24 Sensor
28 Receptacle
130 Container
133 Fluid
134 Base
230 Container
233 Fluid
234 Base
235 Surface 30 Container
31 Inlet
32 Outlet
33 Fluid
34 Base
35 Surface
36 Evaluation circuit
37 Light source
38 Optical detector
4 Phase object
435 Surface
A Laser
B Shutter
C Polarisation filter
D Filter wheel
E Beam splitter
F, H Optical detectors
G Sample holder
α, β Angle
$S_1$, $S_2$ Paths
h Height

The invention claimed is:

1. A method for investigating one or a plurality of phase objects, the method comprising:
   illuminating, with light of a light source, a grid made up of rigid elements, wherein the coherence length of the light source is larger than the average spacing of adjacent rigid elements of the grid;
   generating a diffraction image of the illuminating light scattered on the grid;
   wherein the diffraction image is a Fraunhofer diffraction pattern comprising light maxima at which illuminating light positively interferes;
   placing the one or the plurality of phase objects in the light path between the light source and the grid and/or in the light path of the illuminating light scattered on the grid, wherein the grid generates a diffraction image upon illumination in absence of any phase objects, and wherein the phase objects placed between the light source and the grid and/or in the light path of the illuminating light scattered on the grid change the diffraction image of the grid;
   detecting at least a part of the diffraction image by an optical sensor directly or after interaction with further optical components;
   converting using an optical detector the detected diffraction image or the detected part of the diffraction image into a signal; and
   analyzing the signal to ascertain information relating to the one or plurality of phase objects therefrom.

2. The method according to claim 1, further comprising:
   detecting using the optical detector a temporal sequence of diffraction images or parts of diffraction images and converting the temporal sequence into a sequence of signals; and
   analyzing the sequence of signals to ascertain the information relating to the one or the plurality of phase objects therefrom.

3. The method according to claim 2, further comprising:
   performing, using the sequence of signals, a Fourier analysis of the temporal sequence of the detected diffraction images or of the detected parts of diffraction images, or determining the intensity or fluctuation of the intensity of a part of said diffraction image as a function of time.

4. The method according to claim 1, further comprising:
   simultaneously detecting at least two parts of the diffraction image by at least two mutually spatially separated optical detectors and converting the at least two parts into signals, and
   analyzing the signals to ascertain the information relating to the one or the plurality of phase objects therefrom.

5. The method according to claim 1, further comprising detecting at least the intensity of a primary maximum of the diffraction image by the optical detector.

6. The method according to claim 1, further comprising:
   arranging a transparent protective layer between the grid and the one or the plurality of phase objects, and/or wherein the grid and the phase objects are spaced from one another, and/or wherein the phase objects are disposed in a container that is separate from said grid.

7. The method according to claim 1, in which the phase objects are biological cells or minute animals.

8. The method according to claim 1, further comprising:
   exposing the one or the plurality of phase objects to a substance and/or a physical stimulus; and
   identifying a change of the one or the plurality of the phase objects on the basis of analysis of the signal.

9. The method according to claim 8, further comprising determining, from analysis of the signal, (i) a surface or volume change of the one or the plurality of phase objects, (ii) a process within the one or the plurality of phase objects, (iii) a change of the density of the one or the plurality of phase objects, or (iv) a movement of the one or the plurality of phase objects relatively to the grid.

10. The method according to claim 1, further comprising determining one or more of (i) a level of coverage of the grid by the one or the plurality of phase objects, (ii) a number of phase objects, and (iii) a change of the level of the coverage or of the number of phase objects.

11. The method according to claim 1, in which the diffraction image or the part of the diffraction image is detected at least to some extent in transmission through the grid.

12. The method according to claim 1, in which the diffraction image or the part of the diffraction image is detected at least to some extent in reflection on the grid.

13. The method according to claim 1, in which a characteristic of the one or the plurality of phase objects is ascertained on the basis of the signal, the method further comprising comparing the ascertained characteristic with entries in a database, to ascertain the information relating to the one or the plurality of phase objects.

14. The method of claim 13, wherein said information relating to said one or more phase objects is related to one or more of a level of coverage of the grid by the one or plurality of phase objects, a number of phase objects, a change of the level of coverage or the number of phase objects a movement, a movability, a type, a shape, a surface change, a shape change, a refractive index, a density change, a volume change, a force exerted on the one or the plurality of phase objects, a force exerted by the one or the plurality of phase objects, a substance to which the one or the plurality of phase objects are exposed, a physical stimulus to which the one or the plurality of phase objects are exposed, and a level of intermixing a chemical composition of the one or the plurality of phase objects.

15. The method according to claim 1, wherein there is no chemical bonding between the phase objects and the grid, such that the phase objects can move substantially freely with respect to the grid.

16. A method for investigating one or a plurality of phase objects, the method comprising:

illuminating, with light of a light source, a grid made up of elements, wherein the coherence length of the light source is larger than the average spacing of adjacent elements of the grid;

generating a diffraction image of the illuminating light scattered on the grid;

wherein said diffraction image is a Fraunhofer diffraction pattern comprising light maxima at which illuminating light positively interferes;

placing the one or the plurality of phase objects in the light path between the light source and the grid and/or in the light path of the illuminating light scattered on the grid;

detecting at least a part of the diffraction image by an optical sensor directly or after interaction with further optical components;

converting using an optical detector the detected diffraction image or the detected part of the diffraction image into a signal; and analyzing the signal to ascertain information relating to the one or plurality of phase objects therefrom; and arranging a transparent protective layer between the grid and the one or the plurality of phase objects, and/or wherein the phase objects are disposed in a container that is separate from said grid.

17. The method according to claim 16, further comprising:

detecting using the optical detector a temporal sequence of diffraction images or parts of diffraction images and converting the temporal sequence into a sequence of signals; and analyzing the sequence of signals to ascertain the information relating to the one or the plurality of phase objects therefrom.

18. The method according to claim 17, further comprising:

performing, using the sequence of signals, a Fourier analysis of the temporal sequence of the detected diffraction images or of the detected parts of diffraction images, or determining the intensity or fluctuation of the intensity of a part of said diffraction image as a function of time.

19. The method according to claim 16, further comprising:

simultaneously detecting at least two parts of the diffraction image by at least two mutually spatially separated optical detectors and converting the at least two parts into signals; and analyzing the signals to ascertain the information relating to the one or the plurality of phase objects therefrom.

20. The method according to claim 16, further comprising detecting at least the intensity of a primary maximum of the diffraction image by the optical detector.

21. The method according to claim 16, in which a characteristic of the one or the plurality of phase objects is ascertained on the basis of the signal, the method further comprising comparing the ascertained characteristic with entries in a database, to ascertain the information relating to the one or the plurality of phase objects, wherein said information relating to said one or more phase objects is related to one or more of a level of coverage of the grid by the one or plurality of phase objects, a number of phase objects, a change of the level of coverage or the number of phase objects a movement, a movability, a type, a shape, a surface change, a shape change, a refractive index, a density change, a volume change, a force exerted on the one or the plurality of phase objects, a force exerted by the one or the plurality of phase objects, a substance to which the one or the plurality of phase objects are exposed, a physical stimulus to which the one or the plurality of phase objects are exposed, and a level of intermixing a chemical composition of the one or the plurality of phase objects.

* * * * *